US012308115B2

(12) United States Patent
Reynolds et al.

(10) Patent No.: US 12,308,115 B2
(45) Date of Patent: May 20, 2025

(54) AUTOMATED DATA AGGREGATION WITH FILE ANALYSIS AND PREDICTIVE MODELING

(71) Applicant: Prefcards LLC, Las Vegas, NV (US)

(72) Inventors: Paul Reynolds, Las Vegas, NV (US); Brandon Reynolds, Las Vegas, NV (US); Neil McGuire, Broadway, NC (US); Chad Ramos, Las Vegas, NV (US)

(73) Assignee: Prefcards LLC, Las Vegas, NV (US)

( * ) Notice: Subject to any disclaimer, the term of this patent is extended or adjusted under 35 U.S.C. 154(b) by 355 days.

(21) Appl. No.: 17/694,504

(22) Filed: Mar. 14, 2022

(65) Prior Publication Data
US 2022/0293254 A1 Sep. 15, 2022

Related U.S. Application Data

(60) Provisional application No. 63/254,012, filed on Oct. 8, 2021, provisional application No. 63/160,400, filed on Mar. 12, 2021.

(51) Int. Cl.
*G16H 40/20* (2018.01)
*G06F 3/0482* (2013.01)
(Continued)

(52) U.S. Cl.
CPC ........... *G16H 40/20* (2018.01); *G06F 3/0482* (2013.01); *G06F 40/134* (2020.01);
(Continued)

(58) Field of Classification Search
CPC ..... G16H 40/20; G06F 3/0482; G06F 40/134; G06F 40/166; G06F 3/04842;
(Continued)

(56) References Cited

U.S. PATENT DOCUMENTS

| 2002/0108057 | A1 | 8/2002 | Wu et al. |
| 2004/0237040 | A1 | 11/2004 | Malkin et al. |
| 2009/0234878 | A1* | 9/2009 | Herz ............... H04N 21/252 707/999.102 |

(Continued)

OTHER PUBLICATIONS

U.S. International Searching Authority, International Search Report and Written Opinion received from International Application No. PCT/US22/20236, mailed date Jul. 20, 2022, 10 pages.

*Primary Examiner* — Chad A Newton
(74) *Attorney, Agent, or Firm* — TechLaw Ventures, PLLC; Terrence J. Edwards

(57) ABSTRACT

Systems, methods, and devices for data ingestion and aggregation, file analysis, and predictive modeling. A method includes ingesting an unstructured file comprising text. The method includes providing the unstructured file to a file analysis machine learning algorithm configured to execute optical character recognition processing to identify one or more textual characters in the unstructured file. The method includes assigning the one or more identified textual characters to a data bucket associated with an aggregated data form. The method includes generating a virtual file comprising information from the aggregated data form, wherein the virtual file comprises structured data and unstructured data.

30 Claims, 28 Drawing Sheets

(51) Int. Cl.
  *G06F 40/134* (2020.01)
  *G06F 40/166* (2020.01)
  *G06V 30/14* (2022.01)
  *G06V 30/19* (2022.01)

(52) U.S. Cl.
  CPC ........ *G06F 40/166* (2020.01); *G06V 30/1448* (2022.01); *G06V 30/19173* (2022.01)

(58) Field of Classification Search
  CPC .............. G06F 40/279; G06V 30/1448; G06V 30/19173; G06V 30/153; G06V 30/19013
  See application file for complete search history.

(56) References Cited

U.S. PATENT DOCUMENTS

| | | | |
|---|---|---|---|
| 2010/0161345 A1* | 6/2010 | Cain | G16H 40/20 705/28 |
| 2011/0174755 A1 | 7/2011 | Yamaga et al. | |
| 2011/0208350 A1* | 8/2011 | Eliuk | B01F 35/2209 700/240 |
| 2012/0317472 A1 | 12/2012 | Chernysh | |
| 2013/0311454 A1 | 11/2013 | Ezzat | |
| 2014/0046697 A1* | 2/2014 | Rogers | G16H 10/60 705/3 |
| 2015/0262007 A1 | 9/2015 | Sesum et al. | |
| 2016/0004835 A1 | 1/2016 | Nusimow et al. | |
| 2016/0259902 A1* | 9/2016 | Feldman | G16H 50/20 |
| 2017/0039341 A1 | 2/2017 | Shklarski et al. | |
| 2019/0120929 A1* | 4/2019 | Meadow | H04W 12/06 |
| 2019/0214116 A1* | 7/2019 | Eberting | G16H 40/20 |
| 2020/0176098 A1* | 6/2020 | Lucas | G16H 10/60 |

* cited by examiner

800

≡ Shoulder Arthroscopy — 802

Mark Andrews — 804

Important Note

Gloves : Dr. Andrews: 8 Biogel
Clint (PA) : 7.5 Biogel

- Surgeons
- Facility Info
- Facility Users
- Inventory Manager ▲
- Print PREFcards
- Procedure Costs
- Card Builder
- Notifications

806

812 → Shoulder Arthroscopy | Rename | Copy | Print

Prep/Positioning

Lateral with beanbag, arm tied to IV pole using
Kerlix and Coban
Chloraprep x2
1015 (in shoulder pack)

Notes

Fill up OnQ pump sterile with 400 ml
Ropivacaine on back table

Electrocautery settings

110 Cut/40 Coag

Supplies And Custom Packs — 808

| Name | Reference # | Cost | Open | Hold | Pick |
|---|---|---|---|---|---|
| Argyle Suction Tip | 8888505115 | $0.63 | 0 | 1 | ☐ |
| Arthroscopy Pump Tubing | AR-6410 | $39.00 | | 1 | ☐ |
| Asepto Irrigation Bulb Syringe 60 cc | DYND20125 | $1.49 | 0 | 1 | ☐ |
| Bovie Grounding Pad | BM-ESRSC | $5.40 | 1 | 0 | ☐ |
| Bur Oval HPS 6.0 mm | 60VAL-EL-RH | $60.59 | 1 | 0 | ☐ |
| Coban Wrap 6"x5yd | 30-406 | $12.75 | 1 | 0 | ☐ |
| Cover Mayo Stand 23x55" Sterile | 8337 | $0.92 | 1 | 0 | ☐ |
| Drape surgical Steri-Drape Fenestrated 35x30" Clear Sterile | 1067 | $13.44 | 1 | 0 | ☐ |

810

Copyright © 2013 PREFcards     Tutorials  Home  Contact Us  Terms of Service

Procedure Costs: Shoulder Arthroscopy

Costs by Surgeon / Base Cost Histogram

Show [10] entries  Search:

| Surgeon | Base Cost | Max Cost | Disparity | Links |
|---|---|---|---|---|
| Andrews, Mark | 1291.95 | 1844.72 | 748.48 | PREFcard |
| Sparks, Alex | 998.03 | 1119.49 | 454.56 | PREFcard |
| Murphy, Shawn | 9732.26 | 1101.96 | 429.78 | PREFcard |
| Brown, Clair | 887.73 | 1410.85 | 344.25 | PREFcard |
| Resnick, Morgan | 774.64 | 1950.34 | 231.17 | PREFcard |
| Glass, Aaron | 737.54 | 808.93 | 194.06 | PREFcard |
| Smith, John | 642.16 | 1860.40 | 98.68 | PREFcard |
| Mcqee, William | 558.05 | 1768.83 | 14.57 | |

Sidebar: Surgeons, Facility Info, Facility Users, Inventory Manager, Print PREFcards, Procedure Costs, Card Builder, Notifications Copyright © 2013 PREFcards    Tutorials  Home  Contact Us  Terms of Service

ANDREWS, MARK  
SURGING SURGERY CENTER

SHOULDER ARTHROSCOPY PROCEDURE

IMPORTANT NOTE  
Gloves: Dr. Andrews: 8 Biogel  
Clint (PA); 7.5 Biogel  
PREP/POSITIONING  
Lateral with beanbag, arm tied to IV pole using Kerlix and Coban  
Chloraprep x2  
1015 (in shoulder pack)  
NOTES  
Fill up OnQ pump sterile with 400 ml Ropivacaine on back table  
ELECTROCAUTERY SETTINGS  
110 CUT/40 Coag  
MUSIC  
Heavy metal Spotify station  
SUPPLIES AND CUSTOM PACKS

| Name | Ref # | Cost | Open | Hold | Item Note |
|---|---|---|---|---|---|
| Argyle Suction Tip | 8888505115 | $0.63 | 0 | 1 | Will only use if case converts to open |
| Arthroscopy Pump tubing | AR-6410 | $39.00 | 1 | 0 | |
| Asepto Irrigation Bulb Syringe 60cc | DYND20125 | $1.49 | 0 | 1 | Will only use if shoulder converts to open |
| Bovie Grounding Pad | BM-ESRSC | $5.40 | 1 | 0 | |
| Bur Oval HPS 6.0mm | 60VAL-EL-RH | $60.59 | 1 | 0 | |
| Coban Wrap 6"x5yd | 30-406 | $12.75 | 1 | 0 | |
| Cover Mayo Stand 23x55" Sterile | 8337 | $0.92 | 1 | 0 | |
| Drape Surgical Steri-Drape Fenestrated 35x30" Clear Sterile | 1067 | $13.44 | 1 | 0 | |
| Extremity Surgical T-Drape - Arthroscopy T- Drape | DYNJP8103 | $23.50 | 1 | 0 | |
| Gown Standard Surgical X-Lg St Aami Level 3 | 9536 | $2.87 | 1 | 0 | |
| Instrumental Cannula 7 mm | AR-6550 | $22.50 | 1 | 1 | |
| Kerlix 2.25"x3yd Gauze Cotton Roll | 6720 | $0.74 | 1 | 0 | |
| Laporotomy Sponges 5 count | 6522 | $2.68 | 0 | 1 | Will only use if shoulder converts to open |
| Pencil Tip Bovie | ESPR-EL | $54.65 | 1 | 0 | |
| Pump Kit Pain Relief ON-Q Silver Soaker | P100X2 | $160.00 | 1 | 0 | |
| Shoulder Arthroscopy Pack Custom | SOP40SAAMF | $114.91 | 1 | 0 | |
| Split Sheet with Pouch | 3M-9196-CASE | $28.57 | 1 | 0 | |
| Surgical Blade #11 | 4-311 | $0.28 | 0 | 1 | Will only use if shoulder converts to open |
| Tomcat HC Shaver Blade 4.0 mm | 475-345-000 | $17.00 | 1 | 0 | |
| VAPR VUE 90 electrode | 228147 | $199.00 | 1 | 0 | |

- Surgeons
- Facility Info
- Facility Users
- Inventory Manager ▸
- Print PREFcards
- Procedure Costs
- Card Builder
- Notifications

Inventory Management

| New | Edit | View Usage | Delete |

Search: _____

| | Name ↕ | Reference# ↕ | Cost↕ | Status ↕ | Category ↕ | manufacturer ↕ |
|---|---|---|---|---|---|---|
| ⊙ | #15 Blade x 5 | | 0.00 | Pending | Supplies and Custom packs | |
| ▣ | #2 Fibrewire | | 22.91 | Pending | Sutures | |
| ▣ | #2 Suture Fiberlink Braided PB Blue w/Closed Loop 1.5" | AR-7235 | 50.00 | Approved | Sutures | ARTHREX/TRIBE |
| ✄ | #2,15" Fiberloop w/Straight Needle | AR-7234 | 3.75 | Approved | Sutures | ARTHREX/TRIBE |
| / | #2,38" Fiberwire 2 Strands (1Blue 1White/Black) | AR-7201 | 18.50 | Approved | Sutures | ARTHREX/TRIBE |
| ⌒ | #2,38" Fiberwire Blue w/Needle 26.5mmx.5 circle | AR-7200 | 9.65 | Approved | Sutures | ARTHREX/TRIBE |
| ⌒ | .5ml 12in IV Sterile Latexfree Extension Set | | 4.66 | Pending | Supplies and Custom packs | |
| ⊙ | 0 Ethibond CT-2 x 8 | | 0.00 | Pending | Sutures | |
| ⊙ | 0 Ethibond MO-6 multipack 1 | | 0.00 | Pending | Sutures | |
| ⊙ | 0 PDS CTX 2990G x 2 | | 0.00 | Pending | Sutures | |
| | Search Name | Search inventory | Cost | | | |

Showing 1 to 10 of 2,516 entries

Previous 1 2 3 4 5 ... 252 Next

Notifications

- Surgeons
- Facility Info
- Facility Users
- Inventory Manager
- Print PREFcards
- Procedure Costs
- Card Builder
- Notifications

Show Resloved

Search:

| Title | ↑↓ Date |
|---|---|
| ☐ Gloves | 17 Feb 2021 |

From: Chad Ramos
Surgeon: Mark Andrews
Comment: Dr. Andrews wants 8 1/2 size gloves from now on

[Mark Resloved]

Search Title | | Date

Showing 1 to 1 entries (filtered from 21 total entries) | Previous [1] Next

FIG. 16

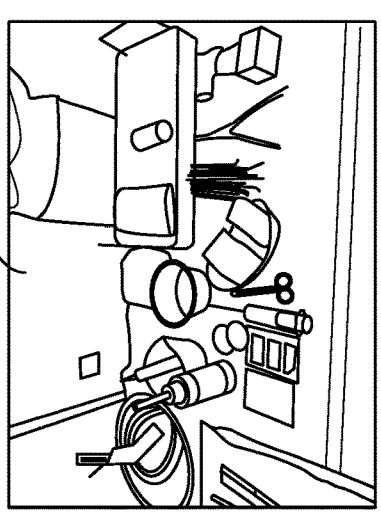

| | | | | |
|---|---|---|---|---|
| ▭ Tourniquet Cuff | $80.40 | 60707010400 | Each | 1 | 0 |
| *Set to 300 mmHg* | | | | |
| ▭ 18 gauge spinal needle | $3.31 | 405184 | Each | 1 | 0 |
| ◯ Surgical Hood | $19.99 | 0408800100 | Each | 4 | 0 |
| ▭ Grounding Pad | $6.50 | E7507 | Each | 1 | 0 |
| ▭ Aquamantys Bipolar Sealer | $499.00 | 23-112-1 | Each | 1 | 0 |
| ▭ 60cc Regular Syringe | $0.68 | 1186000555T | Each | 1 | 0 |
| ▭ ChloraPrep | $5.21 | 260725 | Each | 2 | 0 |
| ▭ Knee Positioner | $31.40 | 803-GP-10 | Pack | 1 | 0 |
| ▭ Dermabond | $178.40 | CLR222US | Each | 1 | 0 |
| ▭ Hemoblast | $249.99 | BQF02-US-SD | Box | 1 | 0 |
| ▭ Knee Immobilizer | $13.37 | 79-80025 | Each | 0 | 1 |
| ▭ Neptune Suction Filter | $80.00 | 700-20 | Each | 2 | 0 |
| ▭ 4 X 4's | $0.06 | NON25416 | Each | 1 | 0 |

▭ Black Table  1710

▭ Prep/Positioning
*Prep:Wipes Knee With Sterile 4x4'x And Alcohol Choraprep X2 1015 No Foley
*Position:Supine Arms On Arm Board  1714

▭ Meds/Dressing
*Medications: Hillock Cocktail (Grab From Pharmacy) Uses Hemoblast Instead Of Surgical Powder
*Dressing : Dermabond Prineo 4x4, 6in Waffle, Vin Double Ace Knee Immobilizer

| 1700 | 1708 | | | |
|---|---|---|---|---|
| Neptune Suction Filter | $80.00 | 700-20 | Each | 2 |
| 4 x4's | $0.06 | NON25416 | Each | 1 |
| Large Royal Silk Gown | $2.68 | 9518 | Each | 1 |
| 3XL Proxima Aurora Gown | $3.00 | DYNJP2712 | Each | 1 |
| ✂ Instruments and Trays | | | | |
| Name | | Ref # | Open | Hold |
| Gelpi | | 204-120 | 0 | 1 |
| *In Set - if Mako Knee* | | | | |
| Z Retractors | | | 0 | 1 |
| *Hold if Mako Knee* | | | | |
| Hillocks Rongeur | | | 1 | 0 |
| Osteotomes | | | 1 | 0 |
| System 6 | | | 1 | 0 |
| Major Ortho Tray | | | 1 | 0 |

* Medications: Hillock Cocktail (Grab From Pharmacy) Uses Hemoblast Instead Of Surgical Powder
* Dressing : Dermabond Prineo 4x4, 6in Waffle, Vin Double Ace Knee Immobilizer 🎵 Music 1716

Bring speaker for Rock Music

🏠 Room Setup 1710

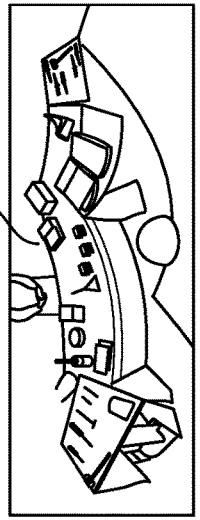

FIG. 17C

| Equipment | | | |
|---|---|---|---|
| Name | | Ref # | Open |
|  Aquamantys Bipolar Sealers | | | 1 |
| Set @ 200 | | | |
|  Armboards | | | 1 |
| Set @ 200 | | | |
|  Tourniquet machine | | | 1 |
| Set @ 350 (Doc does not like the Liner from Tourniquet) | | | |
|  Dornoch | | | 1 |
|  Bovie | | | 1 |
| Set @ 60/60 | | | |
|  Gloves | | | |
| Name | Cost | Ref # | Unit | Open | Hold |
|  7 Protegrity | $0.95 | 2D72NS70 | Pair | 3 | 0 |
FIG. 17D

| Sutures | | | | | |
|---|---|---|---|---|---|
| Name | Cost | Ref # | Unit | Open | Hold |
| 4-0 Monocryl PS-2 | $22.03 | Y496G | Each | 0 | 1 |
| *If Mako Knee* | | | | | |
| 2-0 Vicryl CT-1 | $36.85 | J739D | Each | 1 | 1 |
| 1 Stratafix CTX | $82.57 | SXPP1A400 | Each | 1 | 1 |
| 0 Vicryl CT-1 | $42.62 | VCP840D | Each | 1 | 1 |
| 5 Ethibond V-40 | $54.18 | MB46G | Each | 1 | 0 |
| 3-0 SMP PS-2 | $42.23 | SXMP1B106 | Each | 1 | 1 |

| Implantable Items | | | | | |
|---|---|---|---|---|---|
| Name | Cost | Ref # | Unit | Open | Hold |
| Brasseler Pins | $69.00 | BMA-S90010S | Each | 4 | 0 |
| *Hold If Mako Knee* | | | | | |

JOHN SMITH, MD
ABC Surgery Center

TOTAL KNEE ARTHROPLASTY
PROCEDURE

1818

IMPORTANT NOTE
Surgeon Hints:

*Dr. Smith-8.5 Blue / 9 Esteem 3XL Gown
*Nurse Susan - 7.5 Indicator / 7 Large Gown

* If Mako Knee-No Ioban, Saw Blade or Pins. Uses Gelpis (In Set), 4.0 Monocryl PS-2, Mastisol & Steris for Tib & Femur Incisions. Will Need 1 Batch of Depuy Cement

SUPPLIES AND CUSTOM PACKS

| Name | Ref # | Open | Hold | Item Note |
|---|---|---|---|---|
| Total Knee Pack | DYNJ61480 | 1 | 0 | |
| Bone Cement | 3092-040 | 2 | 0 | |
| Steri Strips | R1547 | 0 | 1 | Only use on Moko Knee coses (for Tib & Femur incisions) |
| Mastisol | 0523-48 | 0 | 1 | Only use on Moko Knee coses (for Tib & Femur incisions) |
| Tourniquet Cuff | 60707010400 | 1 | 0 | Set to 300 mmHg |
| 18 gauge spinal needle | 405184 | 1 | 0 | |
| Surgical Hood | 0408800100 | 4 | 0 | |
| Grounding Pad | E7507 | 1 | 0 | |

PREP/POSITIONING

*Prep: Wipes Knee With Sterile 4x4's And Alcohol Chloraprep X2 1015 No Foley

*Position: Supine Arms On Arm Board

MEDS/DRESSING

*Medications: Hillock Cocktail (Grab From Pharmacy) Uses Hemoblast Instead Of Surgicel Powder

INSTRUMENTS AND TRAYS

| Name | Item Note |
|---|---|
| Gelpi | In Set - If Moko Knee |
| Z Retractors | Hold if Moko Knee |
| Hillocks Rongeur | |
| Osteotomes | |
| System 6 | |
| Major Otho Tray | |

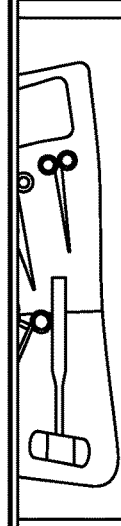
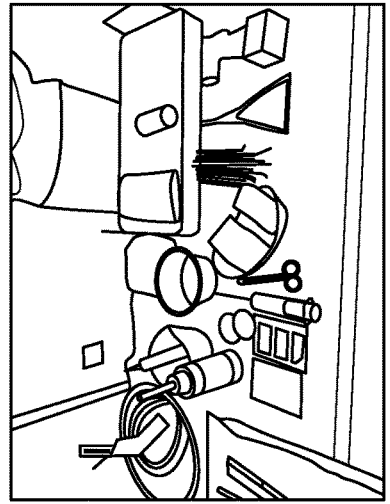

BACK TABLE

EQUIPMENT

| Name | Ref # | Cost | Open | Hold | Item Note |
|---|---|---|---|---|---|
| Aquamantys Bipolar Sealers | | $0.00 | 1 | 0 | Set @ 200 |
| Armboards | | $0.00 | 1 | 0 | Set @ 200 |
| Torniquet machine | | $0.00 | 1 | 0 | Set @ 350 (Doc does not like the Liner from Tourniquet) |
| Domoch | | $0.00 | 1 | 0 | |
| Bovie | | $0.00 | 1 | 0 | Set @ 60/60 |

GLOVES

| Name | Ref # | Cost | Open | Hold | Item Note |
|---|---|---|---|---|---|
| 7 Protegrity | 2D72NS70 | $0.95 | 3 | 0 | |
| 7.5 Indicator | 31275 | $1.74 | 1 | 0 | |

MUSIC

Bring speaker for Rock Music

Last Updated 2021-08-27

Page 1 of 2

FIG. 18B

JOHN SMITH, MD
ABC Surgery Center

TOTAL KNEE ARTHROPLASTY
PROCEDURE

ROOM SETUP

| SUTURES | Ref # | Cost | Open | Hold | Item Note |
|---|---|---|---|---|---|
| 4-0 Monocryl PS-2 | Y496G | $22.03 | 0 | 1 | If Moko Knee |
| 2-0 Vicryl CT-1 | J739D | $36.85 | 1 | 1 | |
| 1 Stratafix CTX | SXPP1A400 | $82.57 | 1 | 1 | |
| 0 Vicryl CT-1 | VCP840D | $42.62 | 1 | 1 | |
| 5 Ethibond V-40 | MB46G | $54.18 | 1 | 0 | |
| 3-0 SMP PS-2 | SXMP1B106 | $42.23 | 1 | 1 | |

| IMPLANTABLE ITEMS | | | | | |
|---|---|---|---|---|---|
| Name | Ref # | Cost | Open | Hold | Item Note |
| Brasseler Pins | BMA-S90010S | $69.00 | 4 | 0 | Hold If Moko Knee |

| MEDICATIONS | | |  |
|---|---|---|---|
| Name | | Open | Hold | Item Note |
| Irrisept | | 1 | 0 | |

Ingesting An Unstructured File Comprising Text.
1902

Providing The Unstructured File To A File Analysis Machine Learning Algorithm Configured To Execute Optical Character Recognition Processing To Identify One Or More Textual Characters In The Unstructured File.
1904

Assigning The One Or More Identified Textual Characters To A Data Bucket Associated With An Aggregated Data Form.
1906

Generating A Virtual File Comprising Information From The Aggregated Data Form, Wherein The Virtual File Comprises Structured Data And Unstructured Data.
1908

FIG. 19

AUTOMATED DATA AGGREGATION WITH FILE ANALYSIS AND PREDICTIVE MODELING

TECHNICAL FIELD

The disclosure relates generally to data aggregation and particularly to data aggregation that leverages file analysis and predictive modeling.

BACKGROUND

Numerous industries rely on consolidated, accurate, and easy-to-understand data. In some cases, this consolidated data may include, for example, a listing of tasks that must be performed, a listing of items to be collected, a recipe to be carried out, and so forth. It can be imperative that the consolidated data is accurate, up-to-date, and easy to maintain when tasks, items, and processes change over time.

Specifically, the healthcare field relies on strict adherence to protocol for successful operation. Healthcare procedures can be particularly complex because they combine efforts of numerous healthcare practitioners within a healthcare facility, and further include the use of pharmaceuticals, medical devices, and other items. Many practitioners and facilities implement the use of "preference cards," or "doctor preference cards" (DPC) when performing a healthcare procedure. Preference cards are used in most operating rooms across hospitals, clinics, and surgical centers. Preference cards function like a recipe card and list the necessary equipment, instruments, and supplies needed for a successful procedure. Preference cards may include specific notes or comments that are meaningful to practitioners and other clinicians to provide the best care. It is important to know exactly which supplies need to be present in the operating room, and when to have those supplies available, to ensure a safe procedure and efficient and accurate billing of the procedure.

Traditional preference cards are handwritten by practitioners, and then a hardcopy of the preference card is stored at each facility where the practitioner performs procedures. Each practitioner may have numerous preference cards, including an independent preference card for each procedure the practitioner performs. Practitioners may additionally have different preference cards at different facilities to reflect the different inventory available at each facility. Practitioners cannot easily amend preference cards, and there is no system that permits practitioners to amend one preference card and then propagate those amendments to other facilities and procedures. Additionally, there is no efficient means for practitioners to share preference cards for certain procedures or provide advice on different items that can be used for a successful procedure.

Additionally, one large facility, such as a hospital or large surgical center, may store thousands of independent preference cards, wherein each preference card is associated with one practitioner and one procedure performed by that practitioner. These facilities cannot easily streamline their preference card system or move to a paperless system because this migration requires manually converting handwritten preference cards to a digital format. This analog-to-digital migration is cost prohibitive because it requires significant time and manpower. Therefore, it is desirable to introduce a streamlined means of ingesting, aggregating, and analyzing data, and then propagating the analyzed data into a file format that is easy to understand and manipulate.

Considering the foregoing, disclosed herein are systems, methods, and devices for data ingestion, unstructured file analysis, and generating preference card files that can easily be updated, synced, and propagated to other systems.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 8 is a screenshot of an example user interface for entering item selections for an aggregated data form;

FIG. 9 is a screenshot of an example user interface for quickly adding item selections to an aggregated data form;

FIG. 12 is a screenshot of an example user interface for providing cost-variation data for a certain procedure;

FIG. 14 is a screenshot of an applicable user interface and virtual file data-output by the data aggregation server;

FIG. 15 is a screenshot of an example user interface of the data aggregation platform;

FIG. 16 is a screenshot of an example user interface of the data aggregation platform;

FIG. 17B is a screenshot of a portion of an example user interface for presenting a virtual file output for an aggregated data form, wherein the portion illustrates an image of requested tools, instructions for positioning, instructions for dressing, and a partial listing of requested supplies;

FIG. 17C is a screenshot of a portion of an example user interface for presenting a virtual file output for an aggregated data form, wherein the portion illustrates an image of a requested room setup, an indication of requested music, and a partial listing of requested supplies;

FIG. 17D is a screenshot of a portion of an example user interface for presenting a virtual file output for an aggregated data form, wherein the portion illustrates a partial listing of requested supplies;

FIG. 17E is a screenshot of a portion of an example user interface for presenting a virtual file output for an aggregated data form, wherein the portion illustrates a partial listing of requested supplies;

FIG. 18B is two screenshots of a virtual file output for presenting an aggregated data form; and FIG. 19 is a schematic process flow diagram of a method for generating a virtual file comprising information retrieved from an aggregated data form.

DETAILED DESCRIPTION

Figure 1A:
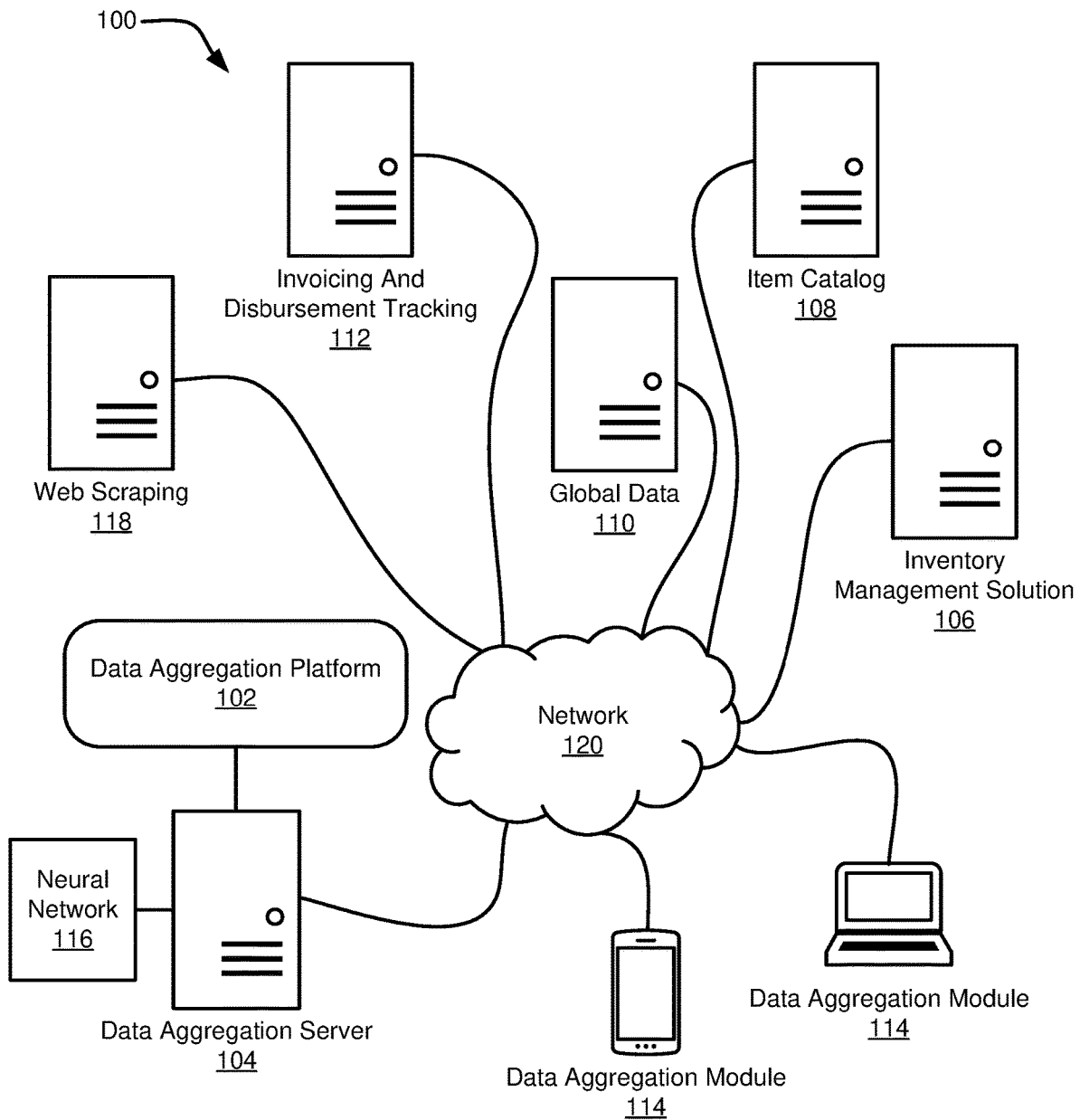
FIG. 1A is a schematic diagram of a system for predictive modeling, file analysis, and management of aggregated data forms.

Disclosed herein are systems, methods, and devices for data ingestion, unstructured file analysis, and generating aggregated data form files that can easily be updated, synced, and propagated to other systems. Additionally, disclosed herein are systems, methods, and devices for predictive modeling and suggesting items to be included in aggregated data form files based on existing inventory, existing products available in the market, historical preferences, historical inventory data, and global information regarding aggregated data forms for medical procedures.

The healthcare industry relies on preference cards when preparing for a procedure. Specifically, hospitals, clinics, and surgical centers rely on practitioner preference cards when selecting items to be present in an operating room for a procedure and when preparing a patient for the procedure. The preference card provides a listing of items that should be ready for use in the operating room before the procedure begins. The preference card may list specific pharmaceuticals, medical devices, instruments, imaging devices, personal protective equipment, and other items that must be present in the operating room for a successful procedure. The preference card may additionally include notes about how the patient should be prepared for the procedure, including how the patient should be positioned and what portions of the patient's body should be exposed for the procedure. The preference card may include notes from the practitioner about how the procedure will be performed, how many support staff should be present for the procedure, and so forth. Preference cards can be critical to good patient care and successful, safe procedures. Additionally, preference cards can be referenced when generating invoices for the procedure to ensure that all items used are accounted for.

Traditionally, preference cards include handwritten notes submitted by practitioners and stored in hard copy at each facility where the practitioner performs procedures. The preference card may be uploaded to a computer system, and still there is no efficient means for the practitioner to alter one preference card and propagate those changes to other facilities where the practitioner performs the same procedure. Additionally, there is no means for practitioners to change one preference card and then propagate that change to other preference cards for different procedures. Additionally, practitioners cannot select items to be included on a preference card based on the available inventory at a certain facility. A practitioner may unexpectedly be provided with different name brands of items, or different products, because the facility does not have the items listed on the practitioner's preference cards. Further, there is no efficient means for practitioners to share preference cards and/or provide guidance or suggestions for updating preference cards based on new products or different means of performing the procedure.

Considering the foregoing, disclosed herein are systems, methods, and devices for efficiently managing aggregated data forms across multiple independent systems. The aggregated data forms described herein may specifically be implemented in a healthcare system for storing preference card data for certain procedures. Further, disclosed herein are systems, methods, and devices for predictive modeling of available item inventory, suggesting alternative items based on historical preference data and outside data sources, and generating accurate billing and invoicing based on up-to-date information.

Before the structures, systems, and methods for generating and maintaining aggregated data forms are disclosed and described, it is to be understood that this disclosure is not limited to the structures, configurations, process steps, and materials disclosed herein as such structures, configurations, process steps, and materials may vary somewhat. It is also to be understood that the terminology employed herein is used for the purpose of describing embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Referring now to the figures, FIG. 1A is a schematic diagram of a system for predictive modeling, file analysis, and data management. The system 100 includes a data aggregation server 104 that supports a data aggregation platform 102. The data aggregation platform 102 may be accessed by a user interface displayed on a data aggregation module 114. The data aggregation server 104 ingests data from one or more independent sources, which may include third-party data aggregation servers, third-party devices, and so forth. The data aggregation server 104 may ingest data pertaining to invoicing and disbursement tracking 112, global data 110, item catalogs 108. The data aggregation server 104 may ingest data directly or indirectly from an inventory management solution 106, which may include one or more robotic components for tracking and disbursing products. The data aggregation server 104 may communicate with and/or include a web scraping component 118 configured to collect structured web data.

The data aggregation platform 102 stores, manages, and updates aggregated data forms. The aggregated data forms discussed herein may specifically be implemented to store data associated with a preference card, such as the surgical procedure preference cards maintained by healthcare facilities. It should be appreciated that the aggregated data forms described herein may be implemented in other industries and implementations, and do not necessarily only include preference card data.

An aggregated data form is a specialized data format comprising a plurality of data buckets. Each data bucket within the aggregated data form is associated with a certain datatype or data content. The aggregated data form stores structured information and unstructured information. In an example implementation, an aggregated data form is a manipulatable data form comprising preference card data. In this implementation, the aggregated data form may comprise text-based data buckets for "provider name," "facility name," "type of procedure," "procedure name," "items to be included at start of procedure," and so forth. Additionally, in this implementation, the aggregated data form includes additional data buckets for receiving unstructured files, such as images, videos, audio files, emails, chat communications, and so forth. These unstructured files are stored with a specific metadata tag in associated with the aggregated data form.

The data aggregation server 104 provides storage and processing resources to support the data aggregation platform 102. The data aggregation platform 102 is a system for executing image analysis algorithms on unstructured files, executing predictive modeling algorithms, storing and managing aggregated data forms, and storing and managing virtual files that represent that data stored within an aggregated data form. In a particular implementation, the data aggregation platform 102 is tuned for storing and managing data pertaining to preference cards, and specifically healthcare preference cards comprising a listing of pharmaceuticals, medical devices, surgical setups, and so forth that are required to successfully perform a healthcare procedure. It should be appreciated that the data aggregation platform 102 may be implemented in other industries and is not necessarily tied to healthcare preference cards. The data aggregation platform 102 includes a user interface that is accessible by way of a website or application by a data aggregation module 114.

The data aggregation server 104 receives input by way of data aggregation modules 114 in communication with the network 120. The data aggregation server 104 communicates with one or more facilities (e.g., hospitals, clinics, surgical centers, and so forth), individual users (e.g., medical personnel, surgeons, hospital administrators, and so forth), and administrators by way of the network 120 connection. The data aggregation server 104 generates independent accounts on the data aggregation platform 102. Each of the independent accounts is assigned to a certain user or entity and includes login information for securely accessing the data aggregation platform 102. In some implementations, one facility might have a global account on the data aggregation platform 102 that may be accessed by certain individuals, and the facility may further have individual accounts that are assigned to certain users, e.g., surgeons, healthcare personnel, administrators, surgical directors, support staff, and so forth. The data aggregation platform 102 can assign permissions for certain accounts to have read and/or write access to certain data. The data aggregation platform 102 also provides accounts to users that are not associated with a facility or other entity, and these accounts may be linked to or synced with other entities. For example, the data aggregation platform 102 enables medical personnel to create an account, enter aggregated data form preferences, and associate those aggregated data forms with certain entities, e.g., certain hospitals or surgical centers that will use the aggregated data forms.

The data aggregation server 104 includes one or more neural networks 116. The data aggregation server 104 may include or communicate with multiple independent neural networks 116 that are trained to perform different tasks. The one or more neural networks 116 each execute a machine learning algorithm configured to perform a certain function.

The data aggregation server 104 communicates with a neural network 116 that performs optical character recognition processing on unstructured files. As discussed herein, this particular neural network 116 may be referred to as the "file analysis neural network" or "file analysis machine learning algorithm." An unstructured file (or unstructured data) includes information that does not have a pre-defined data model or is not organized in a pre-defined manner Unstructured files may be human generated, or machine generated. Examples of unstructured files includes, for example, audio files, video files, images, Microsoft© Word documents, Microsoft® PowerPoint®, emails, chat message logs, data from social networking sites, text messages, locations, call recordings, portable document format (PDF) files, images or scans of hardcopy documents, and so forth.

The file analysis neural network performs optical character recognition processing to identify one or more words or text characters in an unstructured file. The optical character recognition processing techniques include text analysis and text mining. The optical character recognition process analyzes patterns of light and dark portions of an unstructured file to identify letters, numbers, and other characters. The file analysis neural network recognizes characters in various fonts, so the file analysis neural network is trained to correctly classify what it sees in the unstructured file. The file analysis neural network identifies and classifies words and textual characters in computer-generated files (including files comprising various computer-implemented fonts) and human-generated files, including those that are handwritten. The file analysis neural network identifies one or more textual characters within an unstructured file and outputs an identification and classification of those textual characters.

The data aggregation server 104 communicates with a neural network 116 that performs predictive modeling on input data. As discussed herein, this particular neural network 116 may be referred to as the "predictive modeling neural network" or "predictive modeling machine learning algorithm." The predictive modeling neural network predicts future inventory of items that may be included on aggregated data forms. The neural network receives historical item inventory data, global inventory data, and/or global manufacturing data to determine whether certain items might be available at a certain facility. The data aggregation server 104 additionally suggests alternative items in response to determining that a certain item is likely to be unavailable.

The data aggregation modules 114 include computing devices that automatically push data to the data aggregation server 104 and further include computing devices used by a user to manually push data to the data aggregation server 104. The data aggregation modules 114 include any suitable means of data processing and data transmitting, including, for example, personal computers, desktop computers, laptops, mobile phones, smart phones, tablets, video gaming consoles, smart glasses, scanners, cameras, and so forth.

The invoicing and disbursement tracking 112 server includes a system, database, and/or pricing model for items and procedures that may be included on aggregated data forms. The invoicing and disbursement tracking 112 may include an independent server and/or database, or the invoicing and disbursement tracking 112 may be incorporated within the data aggregation server 104. The data aggregation server 104 may communicate with the invoicing and disbursement tracking 112 system by way of an Application Program Interface (API) or other secure means of communication. The invoicing and disbursement tracking 112 system provides up-to-date information on pricing for certain items and services. The invoicing and disbursement tracking 112 system may be facility-specific or may include industry-wide pricing.

In an example implementation, the invoicing and disbursement tracking 112 system is an internal pricing model associated with a facility such as a healthcare system, a healthcare network, a hospital, a surgical center, a clinic, and so forth. The invoicing and disbursement tracking 112 system includes real-time pricing information about items that may be included on aggregated data forms and may further include pricing information for generic or alternative items. The invoicing and disbursement tracking 112 may indicate the facility's cost for certain items and may further indicate the facility's pricing for billing those items to patients. The invoicing and disbursement tracking 112 system may indicate the profit margins for various items. The data aggregation server 104 assesses the pricing and billing information and may provide suggestions to providers regarding the most cost-effective items, the items with the greatest profit margin, and so forth.

The global data 110 server provides information and/or analysis regarding item preferences, items associated with certain procedures, preferences of other healthcare providers, and so forth. In an implementation, the global data 110 includes information about potential shortages of certain pharmaceuticals, medical devices, and other items. The data aggregation server 104 generates item suggestions for accounts associated with the data aggregation platform 102 based on the global data 110.

In an implementation, the data aggregation server 104 receives information from the global data 110 resource about certain medical procedures, and the items associated with those medical procedures. For example, the data aggregation server 104 receives data indicating the items that are commonly used when performing a knee replacement procedure (or any other procedure). The data aggregation server 104 analyzes the data and provides suggestions to accounts on the data aggregation platform 102 that are known to perform knee replacement surgical procedures. The data aggregation server 104 provides information regarding the commonly used items, including exact commercially available versions of those items, the pricing and profit margins for those items, and the predicted availability of those items.

The item catalog 108 includes data regarding certain pharmaceuticals, medical devices, and other items that might be used by users associated with the data aggregation platform 102. The item catalog 108 may include a plurality of databases associated with different manufacturers, wholesalers, and providers of items. The item catalog 108 includes data regarding specific, commercially available items.

The inventory management solution 106 may be associated with a certain healthcare system, healthcare network, healthcare facility, wholesale distributor, manufacturer, and so forth. The inventory management solution 106 may specifically be associated with a hospital, clinic, or surgical center that provides items for use during a procedure based on information provided by the data aggregation platform 102. The inventory management solution 106 tracks the whereabouts and status of various pharmaceuticals, medical devices, and other items within a system.

In an example implementation, the inventory management solution 106 includes sensors, storage facilities, and databases for tracking the current and future locations and status of certain items. The inventory management solution 106 may be associated with a hospital and configured to track the available quantity and the predicted future quantity of certain pharmaceuticals, medical devices, and other items used by the hospital. The inventory management solution 106 includes one or more sensors that are alerted when an item is removed from storage. The inventory management solution 106 includes a database for tracking the location and usage of certain items. For example, when an item is retrieved from storage and delivered to an operating room, the inventory management solution 106 may be notified that the item is currently within the operating room. The inventory management solution 106 stores information regarding whether certain items are immediately available or need to be sterilized, refurbished, or otherwise modified before further use. The inventory management solution 106 tracks the immediate and predicted future availability of disposable or single-use items.

The inventory management solution 106 can be an outside entity or system for inventory management. In an embodiment, the data aggregation server 104 integrates with the inventory management solution 106 by way of SFTP and the inventory management solution 106 delivers flat files at a predetermined cadence. This type of integration has the inventory management solution 106 delivering a flat file with one or more of the following details for inventory visibility, including: device identification, device type, facility name, facility identification, item identification, current inventory, minimum and maximum inventory parameters, expiration data, inventory adjustment types and details, and so forth. The data aggregation server 104 may use the inventory feed to allow users or machine learning algorithms to generate an order to replenish inventory. The data aggregation server 104 may send information to the inventory management solution 106 by way of the SFTP to facilitate restocking at an inventory device. Inventory information is at the point of purchase, as well as in other areas of the data aggregation platform 102.

In an embodiment, the inventory management solution 106 manages multiple locations and stock areas within an ordering location or health system. Some inventory locations utilize hardware and software to support the movement and storage of products. This creates perpetual inventory locations. The data aggregation server 104 interfaces with the hardware and/or software vendors via EDI, API, event monitors, and other means to access key information from the perpetual inventory locations. Information received may include location identifiers, drug product identifiers, current inventory quantity, maximum inventory quantity, minimum inventory quantity, average usage, stock out event, lot, and expiration date. Additionally, the data aggregation server 104 can send information to the hardware and/or software vendors to facilitate restocking inventory at the perpetual inventory device. Using this information, the data aggregation server 104 can generate recommended orders, initial recommended orders, purchase orders, and show system-wide inventory availability and usage. In an embodiment, the data aggregation server 104 has its own electronic perpetual inventory solution that can work with or independently of third-party perpetual inventory solutions and can interface with hardware vendors.

The inventory management solution 106 may include one or more robotic or automated components for counting, tracking, storing, and dispensing products. Such an inventory management solution 106 may be located at a healthcare facility such as a hospital, pharmacy, clinic, and so forth. The robotic or automated components may include a drug cabinet, drug carousel, drug refrigerator, and so forth. The robotic or automated components may include one or more scales for weighing products, scanners, image sensors, processors, and robotic arms for selecting and distributing products. The inventory management solution 106 automatically tracks the inventory that is currently available at the facility and further tracks how much of the inventory is close to expiration. The data aggregation platform 102 may be configured to automatically receive and/or retrieve real-time data from the inventory management solution 106.

In an embodiment, the data aggregation server 104 integrates with the inventory management solution 106 via SFTP and via electronic data interchange (EDI) files strictly for device replenishment. In such an embodiment, the inventory management solution 106 sends an EDI file with one or more of the following details, including: purchase order number, facility or location identifier, device identifier, item identifier, and quantity. The data aggregation server 104 may ingest the EDI file and generate a shopping cart within the data aggregation platform 102 with the necessary items. The data aggregation server 104 sends an EDI file to the inventory management solution 106 indicating any changes to the original EDI file to prepare the device for replenishment.

The data aggregation server 104 communicates with the inventory management solution 106s across a plurality of facilities and institutions. In an example implementation, the data aggregation server 104 communicates with the inventory management solution 106s for various hospitals, surgical centers, item wholesalers, and healthcare systems. The data aggregation server 104 analyzes the data received from the inventory management solution 106 to determine whether a certain item is currently in-stock and available at a certain facility, whether a certain item could be delivered to that facility from a different facility, and/or whether a certain item is likely to be in-stock and ready-for-use at a certain facility in the future. The data aggregation server 104 provides this analysis to certain accounts depending on the needs of those accounts.

The data aggregation platform 102 includes and/or communicates with a web scraping component 118. The web scraping component 118 may be executed by the data aggregation server 104 and/or may be executed by a third-party service that communicates with the data aggregation server 104. The web scraping component 118 collects structured web data in an automated fashion (may also be referred to as web data extraction).

In a particular implementation, the web scraping component 118 is configured to monitor data that may be associated with surgical preference cards. In this implementation, the web scraping component 118 may monitor listings of pharmaceuticals and/or medical devices that have been approved by a government agency such as the Food and Drug Administration in the United States. The web scraping component 118 may monitor listings of pharmaceuticals and/or medical devices, and their respective SKUs and pricing, that are offered by manufacturers, distributers, wholesalers, central healthcare system distributors, and so forth. Additionally, the web scraping component 118 may extract data from preference cards that have been posted publicly on certain websites, message boards, and so forth to identify potential or suggested items or configurations for certain surgeries.

The network 120 includes a computing network that enables the transfer of data between independent processor instances. The network 120 may include a cloud computing network accessible over a wide area network or the Internet. The network 120 may include a local area network.

Figure 1B:
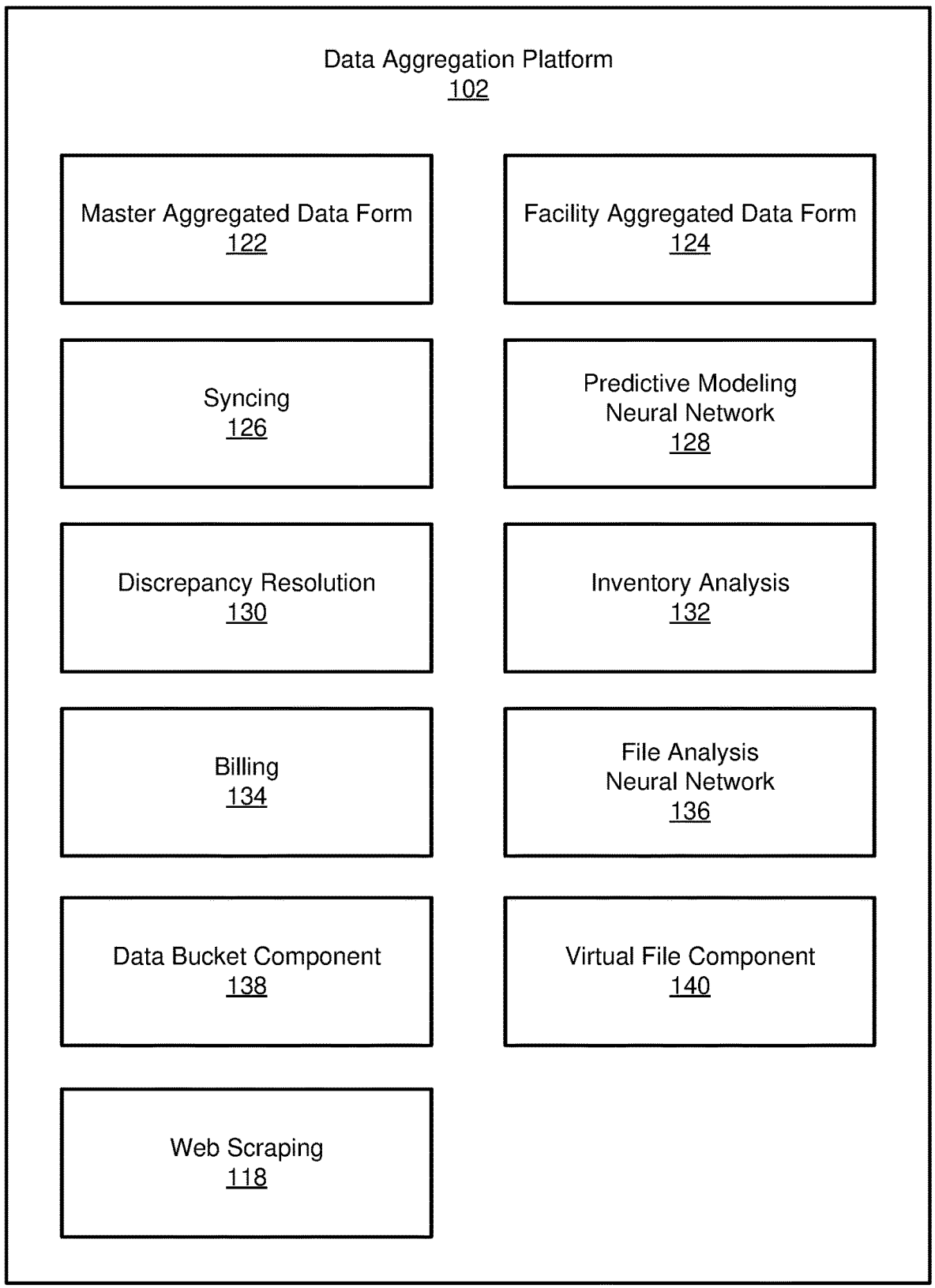
FIG. 1B is a schematic block diagram illustrating components of a data aggregation platform.

FIG. 1B is a schematic block diagram illustrating potential components of the data aggregation platform 102, including processes and modules executed by the data aggregation server 104, and additionally including processes and modules that may be executed by third parties in communication with the data aggregation server 104. The data aggregation platform 102 enables the creation of one or more master aggregated data forms 122 and facility aggregated data forms 124. The data aggregation platform 102 performs syncing 126 of master aggregated data forms and facility aggregated data forms. The data aggregation platform 102 includes a predictive modeling neural network 128 to determine where and when certain inventory items are likely to be available, what inventory items are likely to be most effective for a certain procedure, and what inventory items are likely to serve as suitable replacements for defined preferences. The data aggregation platform 102 performs discrepancy resolution 130 of aggregated data forms with differing item or service selections. The data aggregation platform 102 communicates with inventory management solution 106 and performs inventory analysis 132 of items available at certain facilities. The data aggregation platform 102 communicates with invoicing and disbursement tracking 112 and performs billing 134 analysis and cost prediction. The data aggregation platform 102 includes a file analysis neural network 136 for performing file analysis, including optical character recognition, of unstructured files. The data aggregation platform 102 includes a data bucket component 138 and a virtual file component 140 for managing data stored in association with aggregated data forms, and further for generating output virtual files based on data stored in an aggregated data form.

The data aggregation platform 102 manages the generation and storage of master aggregated data forms 122 and facility aggregated data forms 124. In some implementations, a master aggregated data form is a master preference card associated with a plurality of healthcare facilities, and a facility aggregated data form is a facility preference card associated with a specific facility. It should be appreciated that the aggregated data forms may apply in other industries and circumstances, and do not necessarily include preference card data.

The master aggregated data form 122 component generates and manages aggregated data forms that are not specifically associated with a healthcare facility. The facility aggregated data form 124 components generates and manages aggregated data forms that are associated with a certain facility. The master aggregated data form may be associated with a certain healthcare practitioner or group of healthcare practitioners. A master aggregated data form is assumed to reflect the healthcare practitioner's general preferences for the referenced procedure. When the aggregated data form is associated with a facility, it is then referred to as a facility aggregated data form and represents the healthcare practitioner's preferences when performing the specified procedure at that facility.

The data aggregation platform 102 provides an account associated with a healthcare practitioner. The healthcare practitioner inputs information into the data aggregation platform 102 including, for example, the user's name, healthcare specialty, healthcare network associations, facility associations, healthcare insurance associations, and so forth. The user further indicates the names and/or billing codes for certain procedures performed by the healthcare practitioner, and where the healthcare practitioner performs those procedures. The user may generate an independent aggregated data form for each procedure (these are referred to as master aggregated data forms). The user may further generate in independent aggregated data form for each procedure at certain facilities (these are referred to as facility aggregated data forms). In an example implementation, the user is an orthopedic surgeon, and the user generates an independent master aggregated data form for each procedure the user performs. The user may further generate facility aggregated data forms that indicate different protocols or items the user will use when performing the procedure at a certain facility.

In some implementations, the responsibility to update a facility's aggregated data form falls on the users who relate to that facility, whereas the responsibility to update master aggregated data forms falls on the healthcare practitioner associated with those master aggregated data forms. The facility and/or healthcare practitioner may provide access to aggregated data forms for other persons/accounts to access and update the aggregated data forms on their behalf. Changes will be made to master aggregated data forms and to facility aggregated data forms over time, and these changes are propagated throughout the data aggregation platform 102. The master aggregated data forms 122 are linked to the facility aggregated data forms 124, and vice versa. If the healthcare practitioner implements a change to a master aggregated data form, the healthcare practitioner may choose to push that change out to one or more facilities associated with the master aggregated data form.

When a facility aggregated data form is linked to a master aggregated data form, changes made against the one are propagated as suggested changes to the other. Facility aggregated data forms may be linked to one master aggregated data form, but master aggregated data forms may be linked to multiple facility aggregated data forms, even within the same facility. This allows for changes made by a facility to be floated up to the practitioner's master aggregated data form (and approved by the practitioner), and then proposed as changes to other facility aggregated data forms associated with the same master aggregated data form.

The master aggregated data form 122 and facility aggregated data form 124 components are initiated when a user changes or adds contents to an aggregated data form. This can include generating a new aggregated data form, adding an item, removing an item, changing a quantity of an item, adding, editing, or removing a note, and so forth. A healthcare practitioner may generate a new master aggregated data form at any time. The master aggregated data form has access to "public" inventory, including a listing of items that are maintained and scrubbed regularly by the data aggregation platform 102. This includes, for example, pharmaceuticals, gloves, equipment, imaging devices, robotic devices, computing systems, and so forth. When a new master aggregated data form is created, each facility associated with the healthcare practitioner is notified and given the opportunity to create a linked facility aggregated data form that captures the changes made to the master aggregated data form to stay up to date with the practitioner's preferences.

The data aggregation platform 102 supports one or more user accounts associated with a facility, which may be referred to herein as facility users. A facility user may log on to the data aggregation platform 102 and view a list of practitioners that are associated with the facility. The facility user can see a list of the master aggregated data forms and/or facility aggregated data forms that the facility has for each practitioner. Each facility aggregated data form may be linked to a single master aggregated data form, but more than one facility aggregated data form may be linked to the same master aggregated data form. When the facility creates a facility aggregated data form without a master aggregated data form, the practitioner is offered the opportunity to create a master aggregated data form and link the master aggregated data form to the facility aggregated data form. Otherwise, the practitioner may link the new facility aggregated data form to an existing master aggregated data form. The facility user may also have permission to create a new facility aggregated data form and preemptively link that card to a master aggregated data form.

The data aggregation platform 102 manages the deletion of master/facility aggregated data forms. When a master aggregated data form is deleted, the data aggregation server 104 checks for linked facility aggregated data forms. If a facility aggregated data form is synced to the master aggregated data form that is pending deletion, then practitioner may select a new master aggregated data form to link to the facility aggregated data forms and/or unlink the facility aggregated data forms to the master aggregated data form. The data aggregation platform 102 updates the links on the facility aggregated data forms to the specified master aggregated data form and begins the discrepancy resolution 130 process. In the case of selecting to unlink the facility aggregated data forms, the data aggregation platform removes the links that exist to the facility aggregated data forms for that practitioner, notifies the facilities that have been removed, and provides the facilities the opportunity to correct the issue by linking a facility aggregated data form to the new master aggregated data form.

When a facility aggregated data form is deleted, the data aggregation platform 102 notifies the practitioner that the action has occurred. The data aggregation platform 102 gives the practitioner the opportunity to delete the associated master aggregated data form. This is potentially gated on whether there are other facility aggregated data forms linked to the master aggregated data form at the time.

The syncing 126 component manages push notifications and data syncing across different systems, platforms, facilities, and user accounts. The syncing 126 component may receive an indication that a user modified a master aggregated data form. The syncing 126 component identifies all facility aggregated data forms associated with the master aggregated data form. The syncing 126 component pushes the changes to each of the facility aggregated data forms and may further generate a notification for each of the associated facilities to notify the facilities of the change.

The syncing 126 component manages links between facility aggregated data forms and master aggregated data forms. At times, the data aggregation platform 102 needs to link an existing facility aggregated data form to a master aggregated data form. This may specifically happen when a new system or new facility-user system is set up. This may also occur when the master aggregated data form is modified. When a link is created, the syncing 126 components looks at the differences between the master aggregated data form and the facility aggregated data form. This includes mapping items between inventories, correcting discrepancies in quantities, updating notes, and other conflict resolution processes that occur when comparing the two aggregated data forms. When an item in an aggregated data form is added, changed, or removed, the card's Last Updated Timestamp is updated. This will trigger out-of-sync notifications to linked aggregated data forms.

The syncing 126 component notifies a facility user when there are changes that have been made on an aggregated data form linked to the facility. The facility user may click in to review the changes, and the user interface will populate a list of selected changes to be made to the card. The facility user can review the proposed changes, remove changes, modify changes, and add additional changes. When the facility user is satisfied, the facility user may submit the changes to the target aggregated data form and the relationship will be marked as synced as of the time the batch of changes was submitted. The application or rejection of proposed changes is referred to as "syncing the cards." The aggregated data form includes a "Last Updated" field that indicates a timestamp of the most recent sync cycle.

The syncing 126 component includes a change suggestion engine. The change suggestion engine receives a proposed change and a target card associated with the proposed change. The change suggestion engine suggests what may be done to apply a comparable change to the target card. The change suggestion engine suggests take numerous factors into account when making suggestions, including item names, quantities, types, previously accepted suggestions, rejected suggestions, relationship weights, and so forth. The change suggestion engine proposes a specific action, such as adding a newly created item, editing an existing aggregated data form, editing an existing line-item on an aggregated data form, and so forth. The user may provide feedback, and this feedback is consumed as training data for training the change suggestion engine to make better suggestions. The change suggestion engine may incorporate a neural network.

The predictive modeling neural network 128 component receives information from invoicing and disbursement tracking 112, global data 110, item catalog 108, and/or inventory management solution 106 and predicts the current and future inventory of certain pharmaceuticals, medical devices, and other items. The predictive modeling neural network 128 component may include a neural network trained to identify patterns in item availability and to predict future item availability based on those patterns.

The predictive modeling neural network 128 component may predict whether a certain item will be in-stock and available for immediate use at a certain facility at a time in the future. This analysis is based on historical availability for that item at that facility and may further be based on one or more of the date of the procedure (including the day of week of the procedure), the time of the procedure, the department within the facility where the procedure will be performed, and so forth. The predictive modeling neural network 128 component may predict that the item is unlikely to be available for use at the time of the scheduled procedure. If this is the case, the predictive modeling neural network 128 component may further provide a suggested alternative item that will likely be available at the time of the schedule procedure.

The predictive modeling neural network 128 component predicts future procedures to be performed based on past trends. These predictions consider the seasonality of procedures where significant, for example where certain procedures are more likely to be performed at certain times of the year, certain weeks of a month, certain days of the week, and so forth. The predictive modeling neural network 128 component analyses past procedure information and item usage from those past procedures. The predictive modeling neural network 128 components predicts how many of each item will be used during the procedure. This is a deviation from assuming that each item that was pulled and prepared for the procedure was in fact used during the procedure.

The predictive modeling neural network 128 component may include an analysis of variance (ANOVA) statistical model. ANOVA is a collection of statistical models and their associated estimation procedures used to analyze the differences among means. ANOVA is based on the law of total variance, where the observed variance in a particular variable is partitioned into components attributable to different sources of variation.

The predictive modeling neural network 128 component may include a long short-term memory (LSTM) artificial neural network architecture. LSTM is an artificial recurrent neural network. Unlike standard feedforward neural networks, LSTM has feedback connection. The LSTM architecture can process single data points (such as images) and can further process sequences of data (such as speech or video). The LSTM architecture includes a cell, an input gate, an output gate, and a forget gate. The cell remembers values over arbitrary time intervals and the three gates regulate the flow of information into and out of the cell.

The predictive modeling neural network 128 may include a recurrent neural network (RNN) architecture. The RNN architecture may be particularly implemented for modeling upcoming procedures and predicting future item usage based on past procedures. The RNN architecture is a class of artificial neural networks where connections between nodes form a directed graph along a temporal sequence. This allows the RNN to exhibit temporal dynamic behavior. RNNs can use an internal state (memory) to process variable length sequences of inputs.

The discrepancy resolution 130 component identifies and resolves differences between master aggregated data forms and linked facility aggregated data forms. The discrepancy resolution 130 component resolves differences between linked aggregated data forms. The discrepancy resolution 130 copies from changes from one aggregated data form to another aggregated data form, including items mapped between the cards and quantities of items. The discrepancy resolution 130 component additionally creates a set of changes that would be necessary to bring the aggregated data forms into alignment.

In evaluating the changes, the discrepancy resolution 130 component assesses item mappings that already exist for the facility. If a user has already linked a public item to a facility item, the discrepancy resolution 130 maintains that mapping when comparing the master aggregated data form to the facility aggregated data form. This item mapping allows the discrepancy resolution 130 to recognize matches between items that may not be obvious based on the item names. The data aggregation platform 102 displays a list of changes that have not yet been resolved and allows those changes to be propagated or removed.

For each source action, the discrepancy resolution 130 component defines default behaviors for the target action. Unless otherwise specified, the default action is No Action. When a note is added to an aggregated data form, the discrepancy resolution 130 component checks whether the note's title already exists. If so, the discrepancy resolution 130 component suggests appending the text of the new note.

If there are no notes with the same title, the discrepancy resolution 130 component suggests creating a new note with the text from the linked card. When a note is removed from an aggregated data form, the discrepancy resolution 130 component checks for a note that is either mapped to that note or has the same title. If a duplicate note exists, the discrepancy resolution 130 component suggests deleting the duplicate note.

When a note is updated, the discrepancy resolution 130 component checks for a mapped note or a note with the same title. If such a note exists, the discrepancy resolution 130 component applies the delta to the note's text. If that is successful, the discrepancy resolution 130 component suggests automatically updated the note with the updated text. If it is unsuccessful, the discrepancy resolution 130 requests manual intervention for a user to update the note and presents the original text and permits the user to manually update the text of the note. If there is no mapped note, the discrepancy resolution 130 component suggests that the note be added and provides a user the option to edit the note title or note text.

When an item is added to a master aggregated data form and/or facility aggregated data form, the discrepancy resolution 130 component determines whether there is an item mapping to the target context (i.e., public context or facility context).

The inventory analysis 132 component communicates with one or more inventory management solution 106s and may additionally communicate with one or more of invoicing and disbursement tracking 112, global data 110, or item catalog 108 systems. The inventory analysis 132 component provides suggestions to users based on historical, current, or predicted future inventory at a facility. In an example implementation, the inventory analysis 132 component populates a master aggregated data form and/or facility aggregated data form with items that are known to be available at a certain facility and may additionally provide suggestions for alternate items.

The inventory analysis 132 component additionally communicates with the item catalog 108 to identify specific items that may be included on an aggregated data form. The items may include pertinent information such as manufacturer, cost, supplier, and so forth.

The data aggregation platform 102 exists in at least two contexts, including the public context and the facility context. Items exist within their context (i.e., the public context and/or the facility context) and have data that is specific to that context. The data can be mapped to an item in another context. Any number of public items may be mapped to any number of facility items. Procedure names and procedure billing codes are also mappable items. Item mapping includes a scope. The data aggregation platform 102 maps an item from the public context to the facility context when dealing with a change to an aggregated data form. A user can elect to have the mapping apply only to a certain aggregated data form or to create a more general, facility-level mapping. The data aggregation platform 102 floats card-level mapped items to the top of a drop-down list, followed by facility-level mapped items, followed by non-mapped items from the target context.

The billing 134 component calculates and/or suggests the materials cost for a procedure based on items included on an aggregated data form. The billing 134 component may communicate with outside systems and databases such as the invoicing and disbursement tracking 112 system. The billing 134 component may suggest items based on the wholesale cost and/or the profit margin for billing the use of that item during a procedure. The billing 134 component may provide suggestions to a practitioner user and/or facility user regarding similar items that might reduce cost while providing the same functionality.

The pricing information consumed by the billing 134 component may be retrieved from a public catalog compiled from multiple sources. Each facility in communication with the data aggregation server 104 may additionally provide more accurate pricing for individual items. In some cases, billing is done per-procedure rather than in an itemized fashion for each item used during the procedure. When this is the case, every item wasted comes directly from the bottom line for the procedure. The billing 134 component communicates with the inventory management solution 106 and invoicing and disbursement tracking 112 systems at the facility to retrieve this information and itemize all items used during the procedure. The billing 134 component may communicate with the inventory management solution 106 and/or invoicing and disbursement tracking 112 systems by way of HL7 or other communication standards.

The billing 134 component collects equivalent item designations and recommends using a different item with a lower cost when applicable. The billing 134 component tracks when items are replaced on an aggregated data form and determines whether the item was replaced with an equivalent item. The billing 134 component additional tracks variant pricing between practitioners at certain facilities and across different facilities.

The file analysis neural network 136 identifies objects of interest and textual characters in unstructured data. An unstructured file (or unstructured data) includes information that does not have a pre-defined data model or is not organized in a pre-defined manner Unstructured files may be human generated, or machine generated. Examples of unstructured files includes, for example, audio files, video files, images, Microsoft© Word documents, Microsoft® PowerPoint®, emails, chat message logs, data from social networking sites, text messages, locations, call recordings, portable document format (PDF) files, images or scans of hardcopy documents, and so forth. The file analysis neural network 136 may include one or more independent neural networks that are each trained to perform different types of files analysis. The file analysis neural network 136 may include a neural network trained to identify and/or classify objects of interest within image or video data. The file analysis neural network 136 may include a neural network trained to identify and/or classify words or music recorded in audio data. The file analysis neural network 136 may include a neural network trained to identify textual characters and words in an image, scan, video stream, or other form of unstructured data.

The file analysis neural network 136 includes a machine learning algorithm trained to execute optical character recognition processes to identify one or more words or textual characters in an unstructured file. Textual characters include letters, numbers, punctuation characters, emojis, and other characters. The file analysis neural network 136 is trained to "read" an unstructured file to identify textual characters and/or words within the file, and further to classify the content of the textual characters and/or words within the file.

The file analysis neural network 136 performs optical character recognition to identify one or more textual characters and/or words within an unstructured file. In an example implementation, the unstructured file is an image or a scan of a hardcopy surgical preference card. The hardcopy surgical preference card may include handwritten characters and/or computer-printed characters. The file analysis neural network 136 analyzes the image/scan of the hardcopy surgical preference card and identifies, for example, the name of the surgeon associated with the preference card, the name of the facility associated with the preference card, the name of the surgical procedure, the SKUs and descriptions of the items to be included in the surgical operating room, the quantities of each item to be included in the surgical operating room, the surgeon's preference for certain music to be played during the procedure, and so forth.

Optical character recognition automatically analyzes printed and/or handwritten textual characters and translates those characters into a form that a computer can process and understand. Optical character recognition includes the process of turning a picture or scan of text into text itself, or in other words, translating an image (or other unstructured data file) into a text file, such as a TXT or DOC file. The file analysis neural network 136 is trained on a plurality of vast datasets comprising different fonts, different types of handwriting, different languages, different textual characters, and so forth.

In an implementation, the predictive modeling neural network 128 and/or the file analysis neural network 136 are performed by one or more third-party entities in communication with the data aggregation server 104. In another implementation, the predictive modeling neural network 128 and/or the file analysis neural network 136 are components of the data aggregation server 104 and/or executed by the data aggregation server 104.

The data bucket component 138 assigns data to certain data buckets associated with the aggregated data form. The aggregated data form includes a plurality of data buckets, wherein each data bucket is intended to be associated with data of a certain type and content. In an example implementation, the aggregated data form is a surgical preference card. In this implementation, the aggregated data form may include one data bucket intending to receive one or more images of an example surgical setup and/or operating room. The aggregated data form may additionally include a plurality of data buckets intending to receive textual data regarding, for example, the name of the surgeon or facility, the type of procedure to be performed, the surgeon's preferences, the pharmaceuticals to be present in the operating room, the medical devices to be present in the operating room, and so forth. The aggregated data form may additionally include a plurality of data buckets intending to receive data regarding real-time pricing for medical devices and/or pharmaceuticals, and these data buckets may be in communication with an API or other communication protocol associated with, for example, a manufacturer, distributor, central healthcare system, internal facility inventory management solution, and so forth.

The data bucket component 138 may receive an output from the file analysis neural network 136 comprising one or more textual characters and/or words that were extract from an unstructured file. The data bucket component 138 may then take those textual characters and/or words and assign them to individual data buckets associated with the aggregated data form. For example, if the aggregated data form is a preference card, then the data bucket component 138 may receive a plurality of textual outputs from the file analysis neural network 136 that would read from an image, scan, PDF, etc. of an existing preference card. The data bucket component 138 receives these textual outputs and classifies and/or assigns them to a data bucket within the aggregated data form.

For example, the file analysis neural network 136 may output a name, such as "Dr. Gregory Smith," and then the data bucket component 138 will assign that textual output to the "surgeon name" data bucket. Further for example, the file analysis neural network 136 may output a phrase, such as "knee arthroscopy," and then the data bucket component 138 will assign that textual output to the "procedure name" data bucket. Further for example, the file analysis neural network 136 may output a phrase, such as "tourniquet machine," and then the data bucket component 138 will assign that textual output to an "equipment" data bucket, which comprises a listing of equipment to be present in the operating room during the knee arthroscopy procedure performed by Dr. Gregory Smith, and so forth.

The data bucket component 138 may be automated to classify the content of certain words and phrases. In an example use-case, the data aggregation platform 102 is implemented to aggregate data and maintain data in surgical preference cards. In this example, the data bucket component 138 may consume words and phrases that are known to have significance within a medical vocabulary. For example, each procedure has a name, each medical device has a name, each pharmaceutical has a name, and so forth. When new names and phrases are created, and when new procedures are invented, the data bucket component 138 checks those new names and phrases against known words, phrases, procedure names, medical devices, pharmaceuticals, and so forth. The data bucket component 138 predictively identifies whether the new words or phrases should be classified as, for example, a surgeon, procedure, pharmaceutical, medical device, and so forth. Thus, the data bucket component 138 identifies certain words, phrases, and blocks of text as belonging to a certain data bucket based on the nature of the content, regardless of where those words, phrases, or blocks of text were located on the page of the unstructured file that was analyzed by the file analysis neural network 136.

The virtual file component 140 generates a virtual file output based on data stored in the aggregated data form. The virtual file output may include a formatted electronic document that may be rendered on a graphic user interface of an electronic device or printed in hardcopy format. The virtual file output may include a rendered user interface comprising a web-accessible and editable layout for viewing and manipulating data within the aggregated data form. The virtual file output may include interchangeable data representations, for example, data in JSON or other platform-agnostic structure of data such as binary, XML, and so forth. The virtual file output may include a web-accessible read-only version of the data stored in the aggregated data form, wherein this read-only version of the data may be accessible without authentication. The virtual file output may include a QR code (or other unique code) comprising a URL describing the location of the aforementioned read-only version of the data.

In an example implementation, the virtual file output is a collection of data stored on a server, and this collection of data is accessible on a unique web URL associated with that aggregated data form. In a further example implementation, the virtual file output is a single document, such as a Microsoft® Word document, PDF, video file, image, or another document. In a further example implementation, the virtual file output is a message, such as an email, push notification, audio message, or other communication that communicates the content stored in associated with the aggregated data form.

The web scraping component 118 may be executed by an external third-party service in communication with the data aggregation server 104 and/or may be executed by the data aggregation server 104 itself. The web scraping component 118 performs data extraction for certain types of data across certain web pages. The web scraping component 118 may extract structured data from publicly accessible webpages, and from private webpages necessitating a secure login or connection.

The web scraping component 118 (may alternatively be referred to as a "data scraping" component) identifies, extracts, and saves data retrieved from webpages. The web scraping component 118 additionally "reads" that data and classifies the data based on its content. In an implementation, the web scraping component 118 additionally includes a discrepancy resolution 130 component to determine whether newly retrieved data should replace data that is currently stored on the data aggregation server 104. For example, the web scraping component 118 may identify an updated name, SKU, or other information for a medical device that is stored in associated with the data aggregation platform 102. The discrepancy resolution 130 component then determines whether the currently stored information regarding the medical device should be replaced with the new information extracted by the web scraping component 118.

The web scraping component 118 may communicate directly by way of Hypertext Transfer Protocol (HTTP) and may provide a script execution environment to simulate user interaction. The web scraping component 118 may utilize a web browser process to perform the HTTP communication and execute web scripts designed to render the HTML page for processing. In this case, the web scraping component 118 may execute the scripts it pulls rather than merely receive those scripts as text. This may be necessary on some web pages to enable the web scraping component 118 to convince those web pages that the web scraping component 118 is not a bot, because the scripts are running in a web browser.

The web scraping component 118 caches the content of the web pages its reads and performs additional scraping tasks against those web pages without requiring additional trips to the source web server. This reduces the network traffic and load on the server and may be necessary to obtain the information or to extract additional data.

Figure 2A:
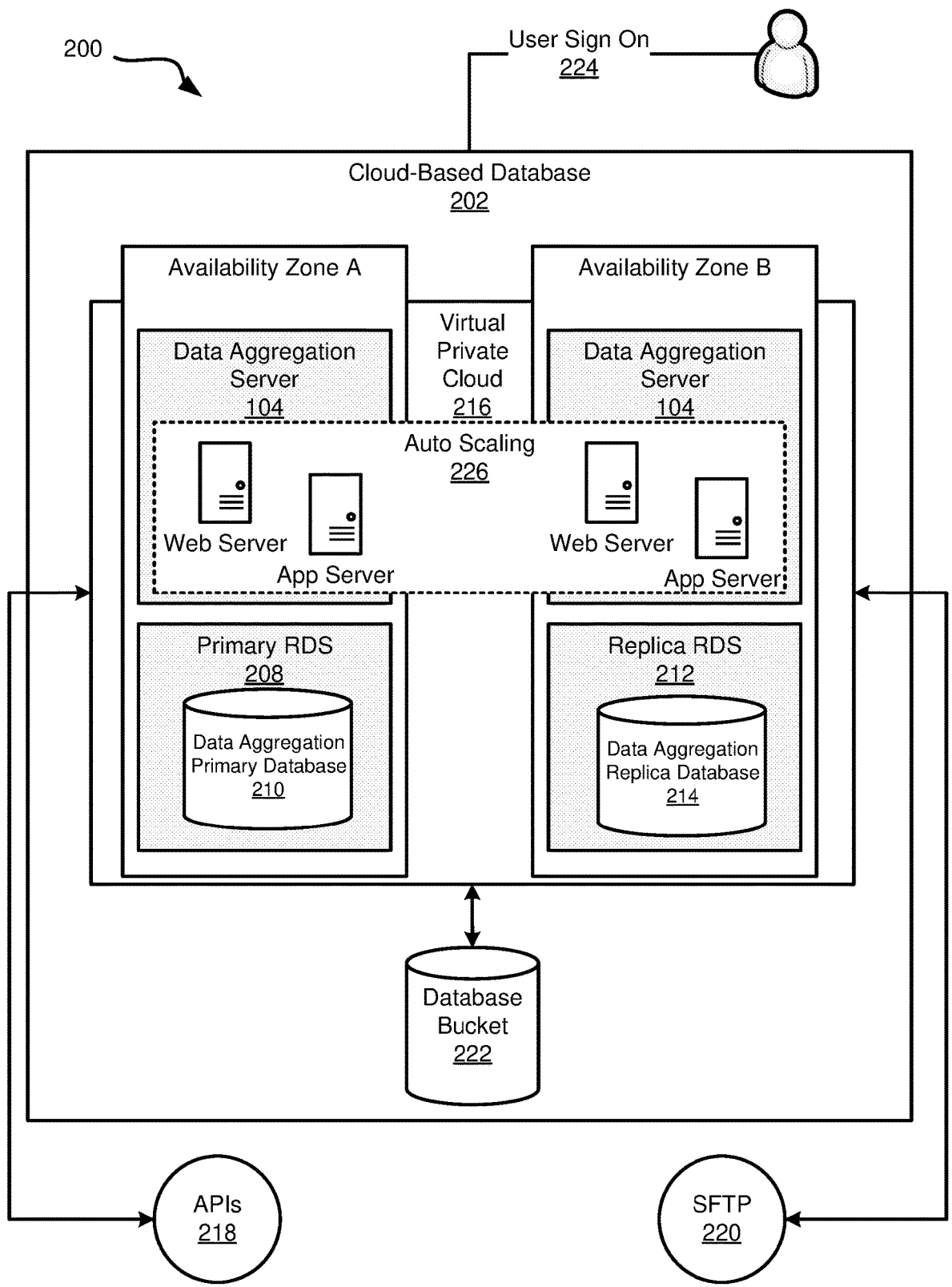
FIG. 2A is a schematic diagram of a system for storing data in a fault-tolerant manner across geographic locations.

FIG. 2A is a schematic block diagram of a system 200 for storing and managing data, such as the systems associated with the data aggregation server 104. The system 200 illustrated in FIG. 2A may be implemented in conjunction with the system 100 illustrated in FIG. 1A. The system 200 includes a cloud-based database 202 supporting the data aggregation server 104. The cloud-based database 202 includes an Availability Zone A and an Availability Zone B. The Availability Zone A includes a first instance of the data aggregation server 104 and the Availability Zone B includes another instance of the data aggregation server 104. Each of the instances of the data aggregation server 104 includes a web server and an app server, and the cloud-based database 202 auto-scales the processing and storage resources between the web servers and app servers for the Availability Zone A and the Availability Zone B. The Availability Zone A includes a primary relational database service (RDS) 208 and the Availability Zone B includes a replica relational database service 212. The data aggregation primary database 210 is stored on the primary relational database service 208 and the data aggregation replica database 214 is stored on the replica relational database service 212. The virtual private cloud 216 of the cloud-based database 202 communicates with outside parties by way of Application Program Interfaces 218 and Secure File Transfer Protocol (SFTP) 220 messaging. The cloud-based database 202 includes a database bucket 222 for storing information associated with the data aggregation platform 102. Users interacting the data aggregation platform 102 can sign on 224 to the service by communicating with the cloud-based database 202.

The cloud-based database 202 includes processing and storage resources in communication with the network 120. The cloud-based database 202 includes a resource manager for managing the usage of processing and storage resources. The resource manager of the cloud-based database 202 performs auto scaling 226 load balancing to ensure adequate processing and storage resources are available on demand based on real-time usage.

The availability zones represent discrete datacenters with redundant power, networking, and connectivity for supporting the data aggregation server 104. The availability zones enable the ability to operate production applications and databases in a more highly available, fault tolerant, and scalable way than would be possible with a single datacenter. The Availability Zone A and Availability Zone B are interconnected with high-bandwidth, low-latency networking, over fully redundant, dedicated metro fiber providing high-throughput, low-latency networking between the availability zones. All traffic between the availability zones is encrypted. The network performance of the availability zones is sufficient to accomplish synchronous replication between the availability zones. Applications, modules, components, and processing methods can be partitioned between the availability zones of the cloud-based database 202. When applications are partitioned across the availability zones, the data aggregation server 104 operates with increased protection and isolation from outages that may be caused by a low in power, hardware issues, software issues, and so forth. The availability zones are physically separated by a meaningful geographic distance to ensure the hardware supporting the availability zones will not be impacted by the same outside forces, such as power outages, natural disasters, and so forth.

The virtual private cloud 216 is an on-demand configurable pool of shared resources allocated within the cloud-based database 202. The virtual private cloud 216 provides isolation between different users communicating with the cloud-based database 202, e.g., different facilities, user accounts, and clients in communication with the data aggregation platform 102. The isolation between one virtual private cloud 216 user and all other users of the same cloud is achieved through allocation of a private IP subnet and a virtual communication construction such as a VLAN or a set of encrypted communication channels per user. The virtual private cloud 216 provides isolation between users within the cloud-based database 202 and is accompanied with a VPN function allocated per-user within the virtual private cloud 216. This secures the remote access to the data aggregation platform 102 by way of authentication and encryption. The data aggregation platform 102 is then essential run on a "virtually private" cloud, even if the processing and storage resources are provided by a third-party cloud-based database service, such as Amazon Web Services®.

The auto-scaling 226 is performed by a resource manager of the cloud-based database 202. The resource manager distributes workload between the web servers and the app servers of the various availability zones of the cloud-based database 202. In some cases, one client of the data aggregation platform 102 may consume a large quantity of storage resources and processing resources at a certain time, and the resource manager will allocate different web servers and app servers across the availability zones to ensure the client receives an adequate quantity of storage and processing resources. The auto-scaling 226 is performed in real-time to meet the needs of the data aggregation platform 102.

The primary and secondary relational database services 208, 212 provide a means to access, replicate, query, and write to the data aggregation database instances 210, 214. The data aggregation primary database 210 may include a copy of data associated with the data aggregation platform 102. The data aggregation replica database 214 may include a replica copy of all or some of the data stored on the data aggregation primary database 210. The replicated databases provide fault-tolerance and protect the data aggregation platform 102 from becoming inoperative during a power outage, hardware outage, or natural disaster.

The database bucket 222 provides object storage through a web service interface. The database bucket 222 uses scalable storage infrastructure that can be employed to store any type of object. The database bucket 222 may store applications, software code, backup and recovery, disaster recovery, data archives, data lakes for analytics, and hybrid cloud storage to support the data aggregation platform 102.

Figure 2B:
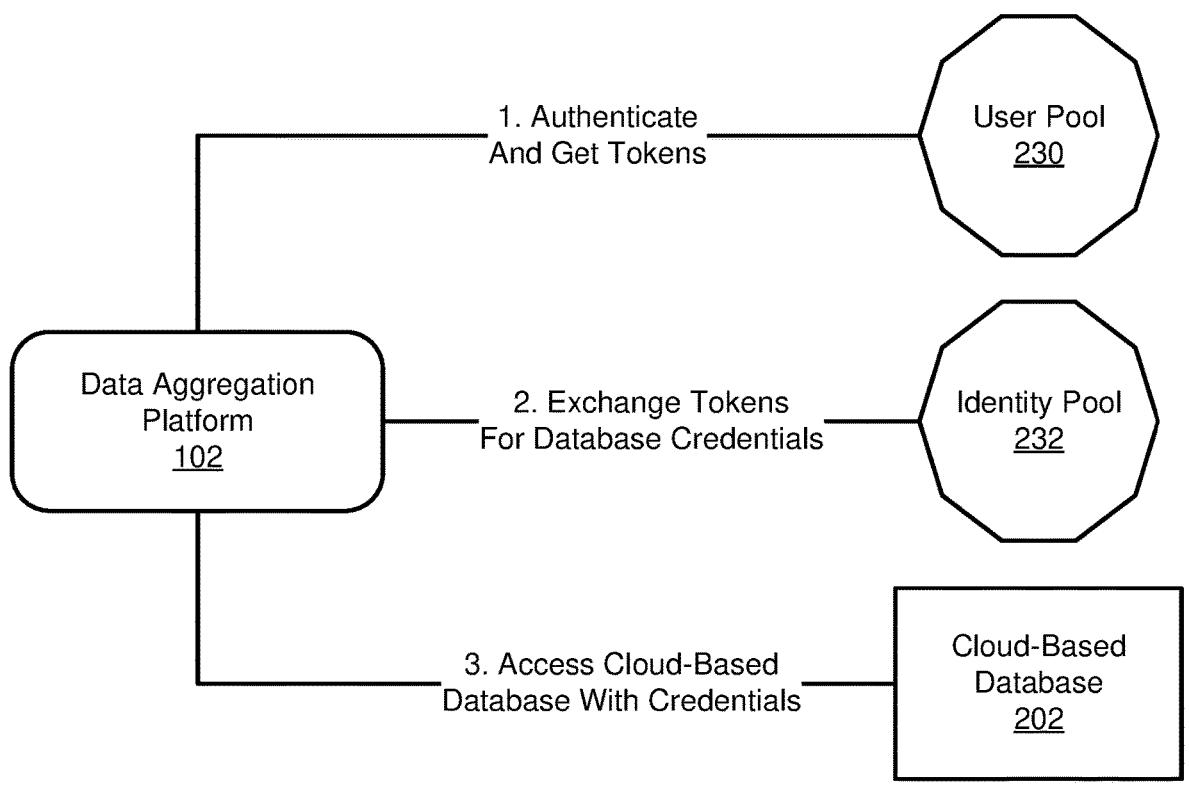
FIG. 2B is a schematic diagram of a system for securely connecting a user with a data aggregation platform based on unique credentials.

FIG. 2B is a schematic block diagram of a system and process flow for accessing the cloud-based database 202 described in FIG. 2A. The data aggregation platform 102 first authenticates and retrieves tokens from a user pool 230. The data aggregation platform 102 then exchanges tokens for database credentials with the identity pool 232. The data aggregation platform 102 is then granted access to the could-based database 202 based upon the credentials.

The user pool 230 is a user directory associated with the cloud-based database 202. With the user pool 230, users can sign into the data aggregation platform 102 through a mobile application, computer-based application, web-based user interface, third-party identity provider, and so forth. Whether users sign in directly or through a third party, all members of the user pool 230 have a director profile that can be accessed. The user pool 230 enables sign-up and sign-in services for the data aggregation platform 102 and further enables social sign-in with outside services, including outside social media networks. The user pool 230 stores a directory, and this directory may be managed, and permissions may be assigned to users within the director.

The identity pool 232 creates temporary credentials to access the cloud-based database 202. The identity pool 232 supports anonymous guest users and social sign-in through outside parties, including third-party social media network.

The system 200 authenticates users by leveraging the user pool 230. After a successful sign-in through the user pool 230, the data aggregation platform 102 creates user pool groups to manage permissions and to represent different types of users. The data aggregation platform 102 creates user groups defined by a type of data permission for that group.

The data aggregation platform 102 may access the cloud-based database 202 through an Application Program Interface (API) Gateway. The API Gateway validates the tokens from a successful user pool 230 authentication and uses those tokens to grant users access to the resources within the data aggregation platform 102 and the cloud-based database 202. The data aggregation platform 102 leverages the user groups defined within the user pool 230 to control permissions with the API Gateway by mapping group membership to roles within the user pool 230. The user groups that a user is a member of are included in the identification token provided by a user pool 230 when the user signs into the data aggregation platform 102. The data aggregation platform 102 submits the user pool tokens with a request to the API Gateway for verification by an authorizer for the cloud-based database 202.

In an embodiment, a unique user pool 230 is created for each tenant within the data aggregation platform 102. This approach provides maximum isolation for each tenant and allows the data aggregation platform 102 to implement different configurations for each tenant. Tenant isolation by user pool 230 allows flexibility in user-to-tenant mapping and allows multiple profiles for the same user. Additionally, in this implementation, a unique hosted user interface may be assigned to each tenant independently, and the data aggregation platform 102 will automatically redirect each tenant to their tenant-specific user interface instance.

In an embodiment, a single user may be mapped to multiple tenants without recreating the user's profile within the data aggregation platform 102. In this embodiment, a data package client is executed for each tenant, and this data package client enables the tenant external IdP as the only allowed provider for that data package client. Data package client-based multi-tenancy requires additional considerations for username, password, and more to authenticate users with the native accounts. When the hosted user interface is in use, a session cookie is created to maintain the session for the authenticated user. The session cookie also provides SSO between data package clients in the same user pool 230.

In an embodiment, the data aggregation platform 102 implements role-based access control. The identity pools 232 assign authenticated users a set of temporary, limited-privilege credentials to access the resources in the cloud-based database 202. The permissions for each user are controlled through roles created within the data aggregation platform 102. The data aggregation platform 102 defines rules to choose the role for each user based on claims in the user's identification token. The rules enable the data aggregation platform 102 to map claims from an identity provider token to a role. Each rule specifies a token claim (such as a user attribute in the identification token from the user pool 230), match type, a value, and a role. The match type can be Equals, NotEqual, StartsWith, or Contains. If a user has a matching value for the claim, the user can assume that role when the user gets credentials. For example, the data aggregation platform 102 may create a rule that assigns a specific role for the users with a custom:dept custom attribute value of Sales.

Rules are evaluated in order, and the role for the first matching rule is used, unless a custom role is specified to override the order. The data aggregation platform 102 may set multiple rules for an authentication provider in the identity pool 232. Rules are applied in order. The order of the rules may be altered. The first matching rule takes precedence. If the match type is NotEqual, and the claim does not exist, then the rule is not evaluated. If no rules match, the role resolution setting is applied to either use the default authenticated role or to deny. The data aggregation platform 102 specifies a role within the API connection to the cloud-based database 202 to be assigned when no rules match in the ambiguous role resolution process. For each user pool 230 or other authentication provider configured for an identity pool 232, the data aggregation platform 102 may assign numerous rules.

Figure 3:
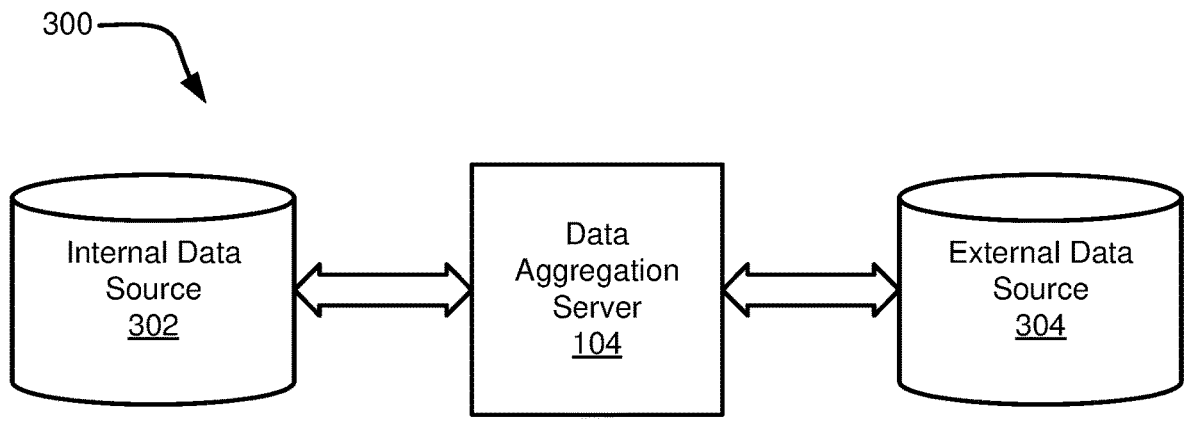
FIG. 3 is a schematic diagram of a system for data communication between a data aggregation server and internal and external data sources.

FIG. 3 is a schematic diagram of a system 300 for data communication between a data aggregation server 104 and internal and external data sources. The data aggregation server 104 identifies and quantifies the availability and cost of items based on outside data. Specifically, the data aggregation server 104 may receive information regarding, for example, items available on the market for purchase, the pricing of items, items currently available at a facility, the status of items held by a facility, the profit margin for billing the use of items to a patient, the efficacy of certain items, third-party reviews, and opinions about certain items, and so forth. The data aggregation server 104 may communicate with one or more of an internal data source 302 and an external data source 304.

In an embodiment, the data aggregation server 104 communicates directly with an external data source 304 that is managed or owned by a third-party entity. The data aggregation server 104 may communicate by way of SSL-encrypted HTTP connections. In an embodiment, the external data source 304 is a relational database, and the data aggregation server 104 communicates with the relational database by way of an Application Program Interface (API). In an embodiment, the external data source 304 is an encrypted hard drive that has been shared with the data aggregation server 104. In an embodiment, the external data source 304 is a virtual data center, and the data aggregation server 104 access the data on a virtual server after signing in or undergoing some other authentication step.

In an embodiment, the data aggregation server 104 communicates with an internal data source 302 that is not managed by some other third-party entity. The internal data source 302 may include a file that has been downloaded or otherwise received from some third-party entity. After the file has been downloaded, the file can be managed and manipulated by the data aggregation server 104. The internal data source 302 may include an encrypted hard drive that is provided by a third-party.

In an embodiment, the data stored in the internal data source 302 has been "cleaned" or pared down to only include necessary or critical information. This can be beneficial to ensure the totality of the data is a usable size that can be efficiently queried, analyzed, and manipulated. For example, the raw data retrieved from the external data source 304 may include numerous data fields that are not necessary for generating and maintaining aggregated data forms as described herein. The unnecessary data may be eliminated, and only the necessary data may be stored on the internal data source 302. In an embodiment, the raw data is cleaned and stored in a relationship database.

The data aggregation server 104, or some other module in communication with the data aggregation server 104, may create intermediary files or tables within a relational database. The intermediary files or tables may include certain information columns that are pertinent to answer a specific question, such as whether an item is owned by a certain facility. This can be beneficial to ensure that each intermediary file or table is no bigger than it needs to be to include all necessary information for answering the specific question. This decreases the amount of disc storage and/or Random-Access Memory (RAM) needed to analyze the information and calculate the answer to the specific question.

Figure 4:
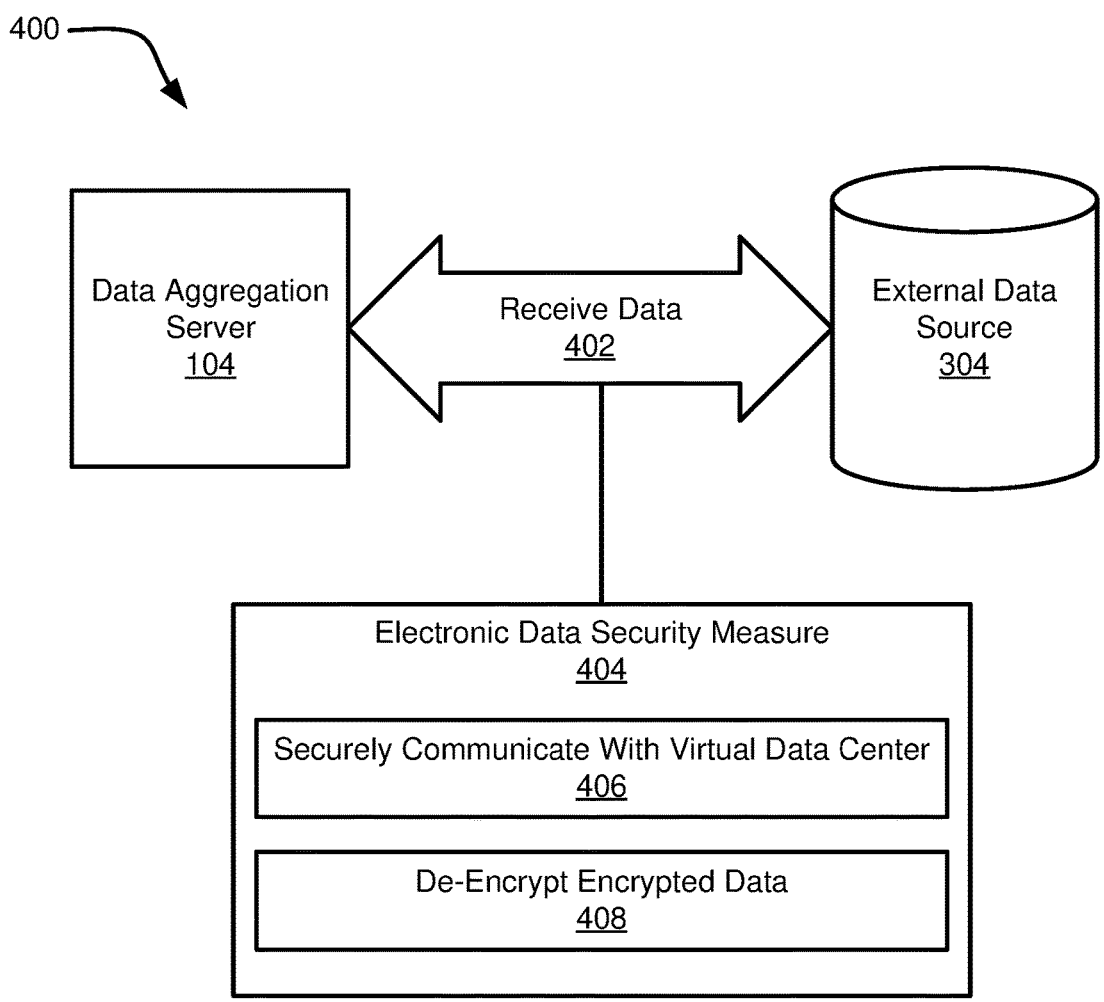
FIG. 4 is a schematic diagram of a system for performing electronic data security measures on data received from an external data source.

FIG. 4 is a schematic diagram of a system 400 for performing electronic data security measures on data received from the external data source 304. The data aggregation server 104 receives claims data (see 402) from an external data source 304. In some cases, the data may be private or encrypted, such as item-use data for procedures that were performed in the past. This data may be received as part of a healthcare claim and may include private or personal information.

In an embodiment, the data aggregation server 104 may receive data by securely communicating with a virtual data center. The virtual data center may be provided by a private or public healthcare entity. In an embodiment, an account may be created for a user associated with the data aggregation server 104, and the user could sign into the virtual data center with the account. The user could then access the data stored in the virtual data center by way of the account. The data may be encrypted or non-encrypted based on the security measures of the virtual data center. In an embodiment, the data may be non-encrypted when viewed by way of a network connection, and the data may be encrypted if downloaded for offline use and manipulation. If the data is downloaded in an encrypted form, then the data must be de-encrypted prior to analysis and manipulation.

In an embodiment, the data aggregation server 104 receives data by way of an encrypted hard drive. The encrypted hard drive may be provided by the source of the data, such as private or public healthcare entity. In an embodiment, the data aggregation server 104 receives claims data by way of an encrypted file that has been downloaded by way of a network connection. The data aggregation server 104 undergoes an electronic data security measure 404 by de-encrypting the claims data.

Figure 5:
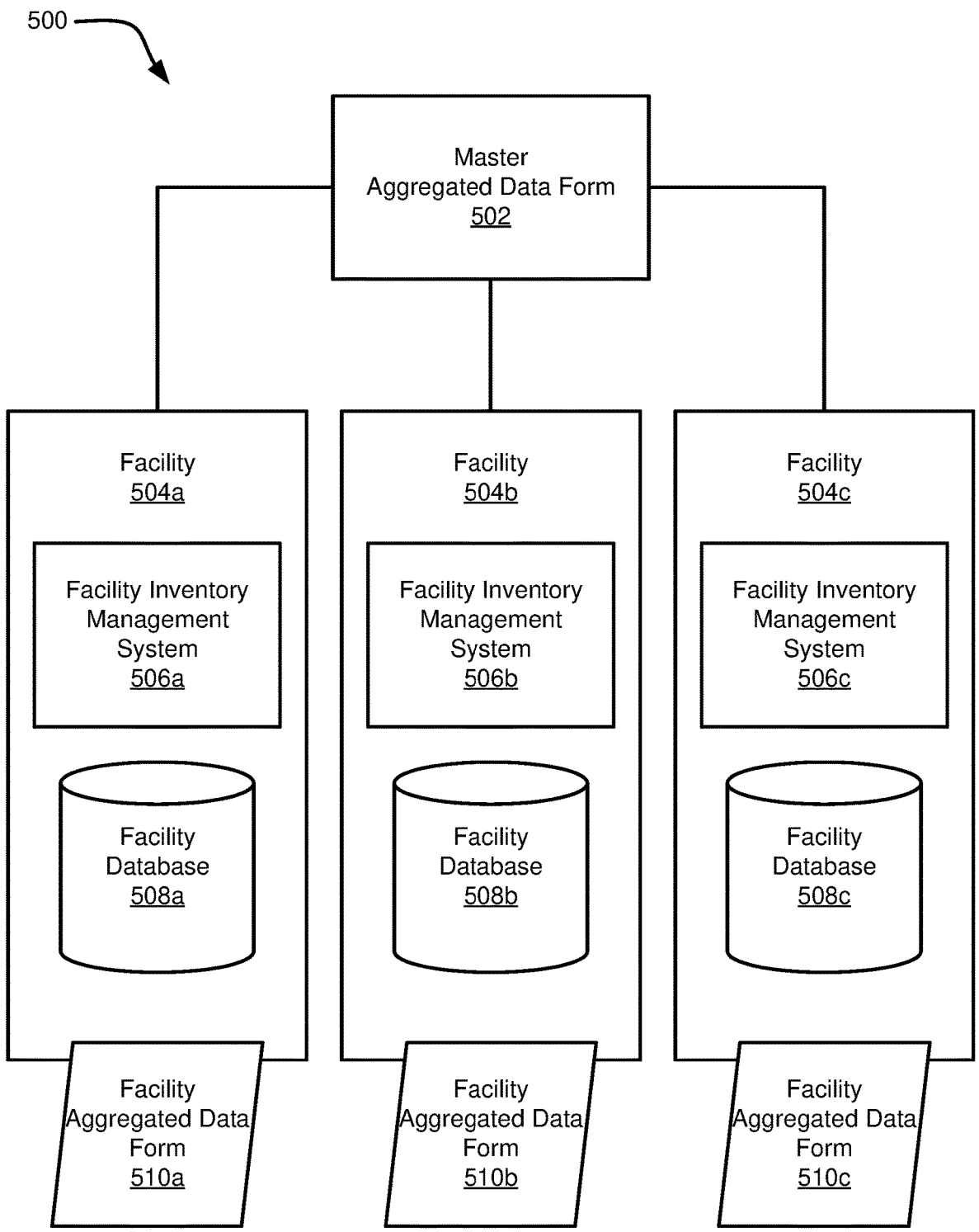
FIG. 5 is a schematic block diagram of a system and method for applying a master aggregated data form to one or more facilities.

FIG. 5 is a schematic block diagram of a system 500 and method for applying a master aggregated data form 502 to one or more facilities 504a, 504b, 504c (may be generically referred to herein as facility 504). The data aggregation server 104 communicates with facility inventory management systems 506 (see 506a, 506b, 506c) associated with different facilities 504. The data aggregation server 104 additionally communicates with one or more facility databases 508 (see 508a, 508b, 508c) associated with those facilities 504. The data aggregation server 104 suggests edits to the master aggregated data form 502 based on the inventory data and facility data received from the facilities 504. These suggested edits may be reflected in the facility aggregated data forms 510 (see 510a, 510b, 510c) for each of the different facilities 504. As discussed herein, the "facility aggregated data forms" 510 may alternatively be referred to as "slave aggregated data forms" to refer to the master-slave data architecture.

Traditionally, the healthcare industry implements the HL7 standard system, and this system does not have any specifications for the management of aggregated data form data. The data aggregation server 104 may communicate with existing systems by way of custom-built APIs to retrieve real-time data from the existing systems. The data aggregation server 104 may retrieve inventory lists through the HL7 interface. The aggregated data form system 104 analyzes changes made against a facility card and pass it up to the master card for evaluation by the practitioner, since the request may have happened at the practitioner's request, and this would allow them to apply the change more broadly than just at the one facility.

Figure 6:
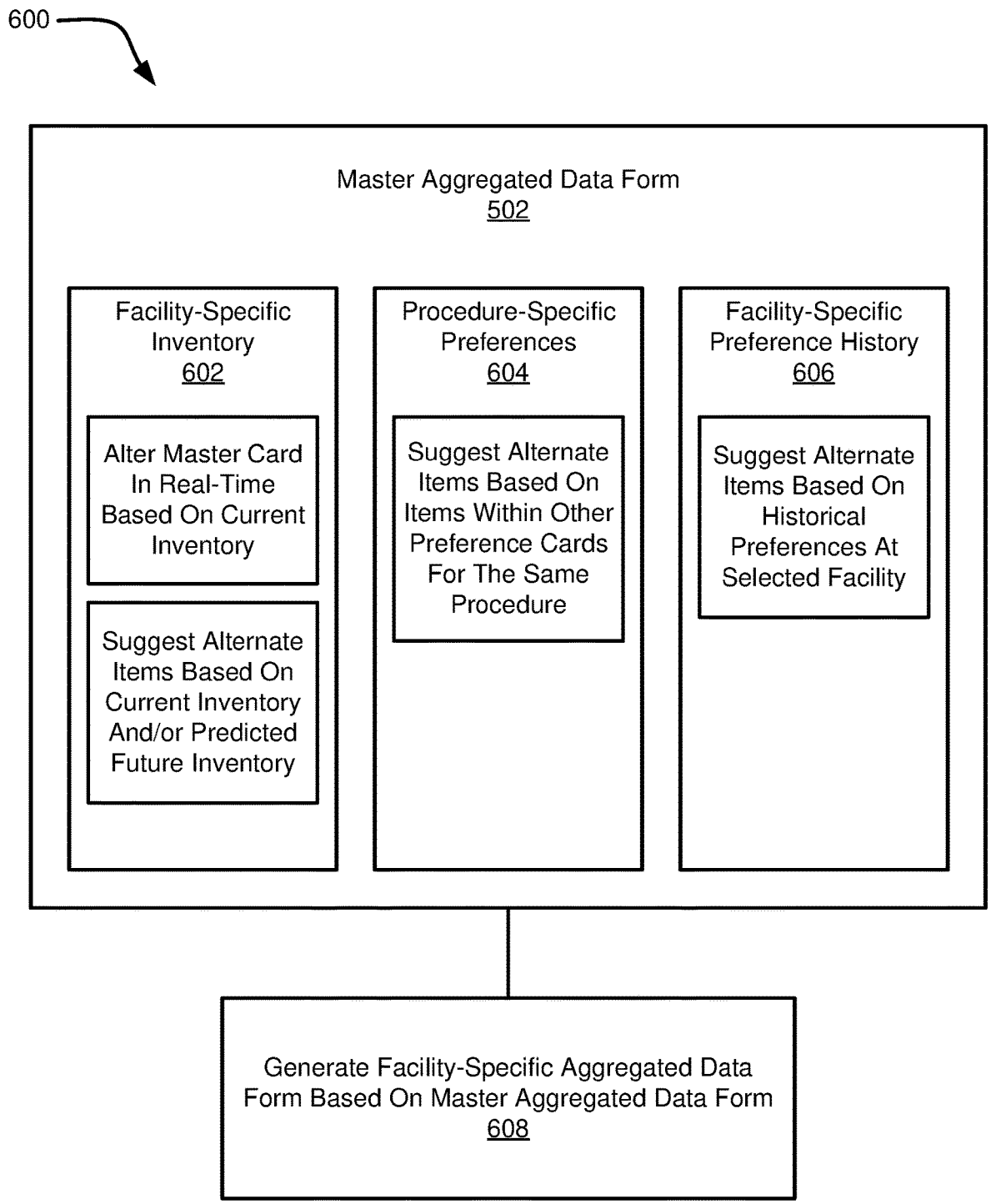
FIG. 6 is a schematic block diagram of a process flow for generating and suggesting procedure-specific and/or facility specific aggregated data form items based on a master aggregated data form and additional data sources.

FIG. 6 is a schematic block diagram of process flow 600 for generating and suggesting procedure-specific and/or facility-specific aggregated data form items based on a master aggregated data form and additional data sources. The process flow 600 illustrated in FIG. 6 may be performed by a neural network, wherein the neural network is trained on datasets comprising aggregated data forms for healthcare practitioners across numerous facilities and geographical areas, along with real-time data applicable to items that may be used in aggregated data forms.

The master aggregated data form 502 is generated by a practitioner. The data aggregation server 104 analyzes the items selected in the aggregated data form, along with the procedure associated with the aggregated data form, and the facilities where the procedure will be performed, and provides one or more suggestions for amending the master aggregated data form 502. The data aggregation server 104 analyzes facility-specific inventory 602, which may include altering the master card in real-time (or suggesting amendments) based on current inventory of items at a facility where the procedure will be performed. This may additionally include suggesting alternate items based on current inventory and/or predicted future inventory.

The data aggregation server 104 analyzes procedure-specific preferences along with the item catalog 108 and may provide suggestions on alternate items for the applicable procedure. The data aggregation server 104 may receive information from other practitioners performing the same procedure, reviews written about items in the item catalog, and information in the item catalog indicating that certain items can be used for the applicable procedure. The data aggregation server 104 suggests to the practitioner that alternate items may be used in the applicable procedure. In an implementation, the practitioner may request suggested items for an applicable procedure, and the data aggregation server 104 determines the suggested items based on other aggregated data forms within the system for the same procedure and/or publicly available aggregated data forms for the applicable procedure.

The data aggregation server 104 may additionally analyze facility specific preference history 606 and suggest alternate items based on the practitioner's historical preferences at a selected facility. The practitioner and/or the facility may manually input the practitioner's preferences at that facility. The data aggregation server 104 may identify these preferences based on data indicating what products the practitioner used when performing procedures at the facility.

The data aggregation server 104 analyzes items on other aggregated data forms that are used for similar or identical procedures. The data aggregation server 104 determines whether the aggregated data form includes specific items that require other items to be present to be used. This is the case when, for example, there is a disposable piece to be used in operating a piece of machinery, or in the case of a supply that is necessary to the use of the equipment, such as jelly for the use of an ultrasound. The data aggregation server 104 references outside data, such as the manufacturers' recommendations, studies on outcomes of the use of different items, and what other practitioners in the field are using based on their own aggregated data forms.

Figure 7:
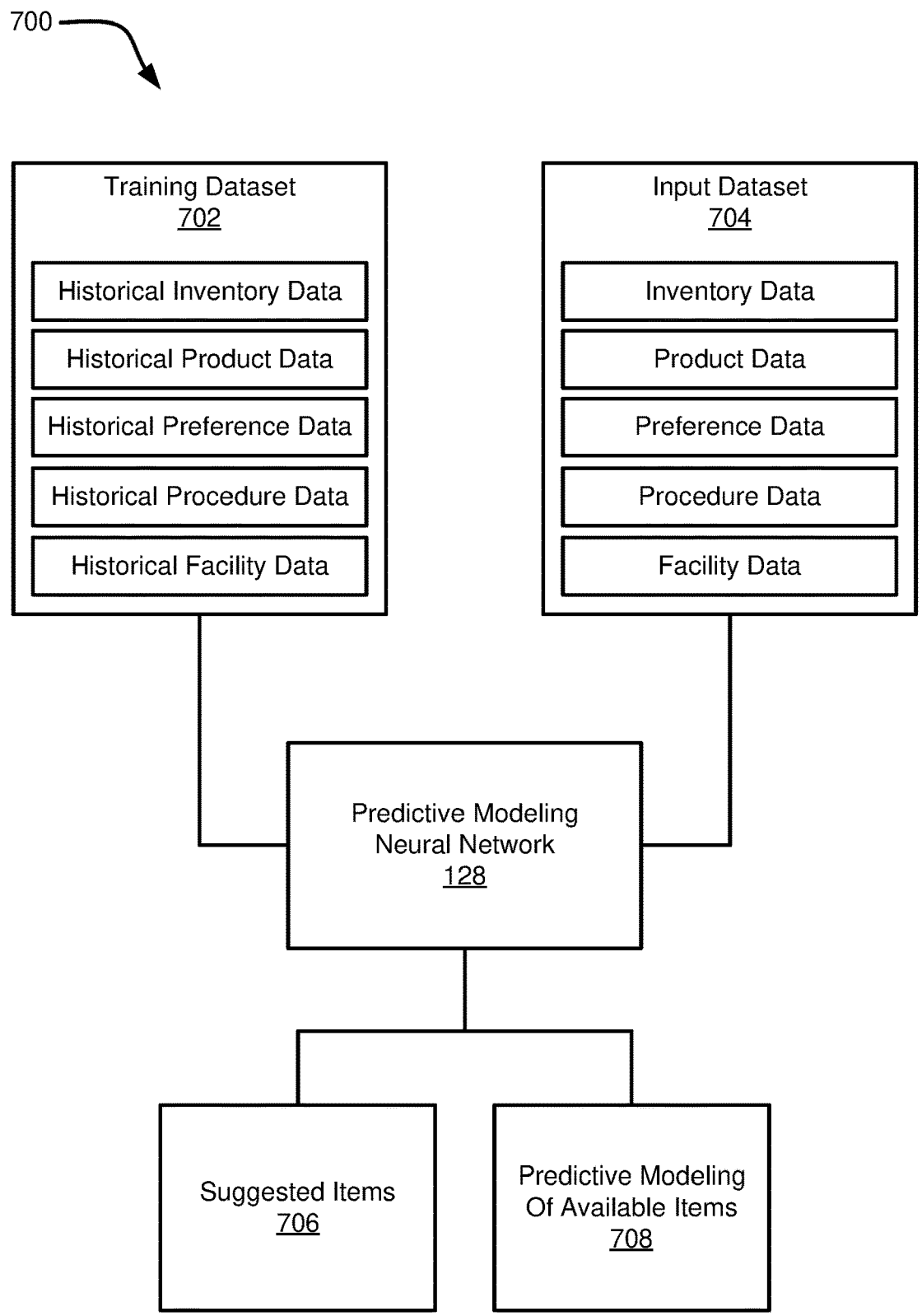
FIG. 7 is a schematic block diagram of a dataflow for training a neural network, providing input data to the neural network, and receiving an output calculation from the neural network.

FIG. 7 is a schematic block diagram of a dataflow 700 for training a neural network, providing input data to the neural network, and receiving an output calculation from the neural network. The neural networks described herein may be trained based on a training dataset 702 including one or more of historical inventory data, historical product data, historical preference data, historical procedure data, and historical facility data. When the neural network is trained, the neural network may be configured to perform real-time analysis on data within an input dataset 704, including one or more of inventory data, product data, preference data, procedure data, and facility data. These datasets are fed to the predictive modeling neural network 128. The predictive modeling neural network 128 outputs one or more of suggested items 706 of an aggregated data form and/or predictive modeling of available items 708 based on the input data.

FIG. 8 is a screenshot of an example user interface 800 for entering item selections for an aggregated data form. The screenshot indicates that a listing of available items may be presented to the user, and the user may select any quantity of the listed items as applicable for the procedure. The listed items may be pulled in real-time from one or more of an inventory management solution 106 and/or the item catalog 108.

In the example illustrated in FIG. 8, the user interface 800 is rendered to illustrate components of a surgical preference card, and further to enable a user to edit the surgical preference card. In this example implementation, the user interface 800 includes a procedure title 802, and in the example user interface 800 illustrated in FIG. 8, the aggregated data form is associated with a shoulder arthroscopy. The user interface 800 includes a practitioner name 804, and in this case, the practitioner (surgeon) is Mark Andrews.

The user interface 800 includes an accessible menu 806 comprising a plurality of options, including, for example, "Surgeons," "Facility Info," "Facility Users," "Inventory Manager," "Print Preference Cards," "Procedure Costs," "Card Builder," and "Notifications." Each of the items within the accessible menu 806 is an interactive button that may be selected by a user. When a user selects the interactive button, the user interface 800 will redirect and enable the user to view and/or amend additional information relating to the selected menu item. The accessible menu 806 may remain accessible at one portion on the user interface 800 while the user interacts with other portions of the user interface 800. For example, the accessible menu 806 may be "locked" and remain accessible at the left-hand sidebar (as shown in FIG. 8), on the right-hand sidebar, on the top of the user interface 800, and/or on the bottom of the user interface. The accessible menu 806 may remain visible and accessible even when the user scrolls the user interface 800.

The user interface 800 includes an input box 808. In the implementation illustrated in FIG. 8, the input box 808 displays an "Important Note" regarding the preference card, and specifically indicates the name of the surgeon, the gloves preferred by the surgeon, the name of the physician assistant, and the gloves preferred by the physician assistant. It should be appreciated that the input box 808 may display any suitable information depending on the implementation. The user may interact with the input box 808 to amend the information that is displayed therein.

The user interface 800 includes a dynamic list 810. The user interface 800 may include a plurality of different dynamic lists 810 each associated with a different topic. In the implementation illustrated in FIG. 8, the dynamic list 810 includes a listing of products under the grouping of "Supplies And Custom Packs." The product listing is dynamic and editable such that a user may quickly alter the items within the product listing, alter the quantity of each item within the product listing, delete items from the product listing, and see real-time up-to-date information regarding each item within the product listing. The dynamic list 810 illustrated in FIG. 8 includes, as an example, "Argyle Suction Tip," "Arthroscopy Pump Tubing," "Asepto Irrigation Bulb Syringe 60 cc," "Bovie Grounding Pad," "Bur Oval HPS 6.0 mm," "Coban Wrap 6"×5 yd," "Cover Mayo Stand 23×55" Sterile," and "Drape Surgical Steri-Drape Fenestrated 35×30" Clear Sterile." It should be appreciated that the dynamic list 810 may include a listing of any suitable items, including, for example, products, names of people, names of places, appointments, tasks to be performed, and so forth.

In an embodiment, the dynamic list 810 is automatically updated in real-time based on information retrieved by the data aggregation server 104, including, for example, data from the web scraping component 118, data from the invoicing and disbursement tracking 112 server, global data 110, item catalog 108 data, and data from the inventory management solution 106. The data aggregation server 104 may automatically update the dynamic list 810 to indicate, for example, that the SKU for an item has changed, the pricing for an item has changed, the quantity available of an item has changed, and so forth.

The user interface 800 includes update input boxes 812 wherein a user may amend or update information displayed on the user interface 800. The update input boxes 812 may include, for example, a button enabling a user to change the name of a procedure, surgeon, item within the dynamic list 810, and so forth. The user interface 800 further enables a user to print, copy, or save information illustrated in the user interface 800.

The user interface 800 may flag certain items within the dynamic list 810. In the example illustrated in FIG. 8, the shaded grey portion for "Bur Oval HPS 6.0 mm" indicates that the item has a cost higher than a threshold configurable by the facility. This enables the facility to easily identify items that are the largest contributors to the cost of the procedure.

Figure 9:
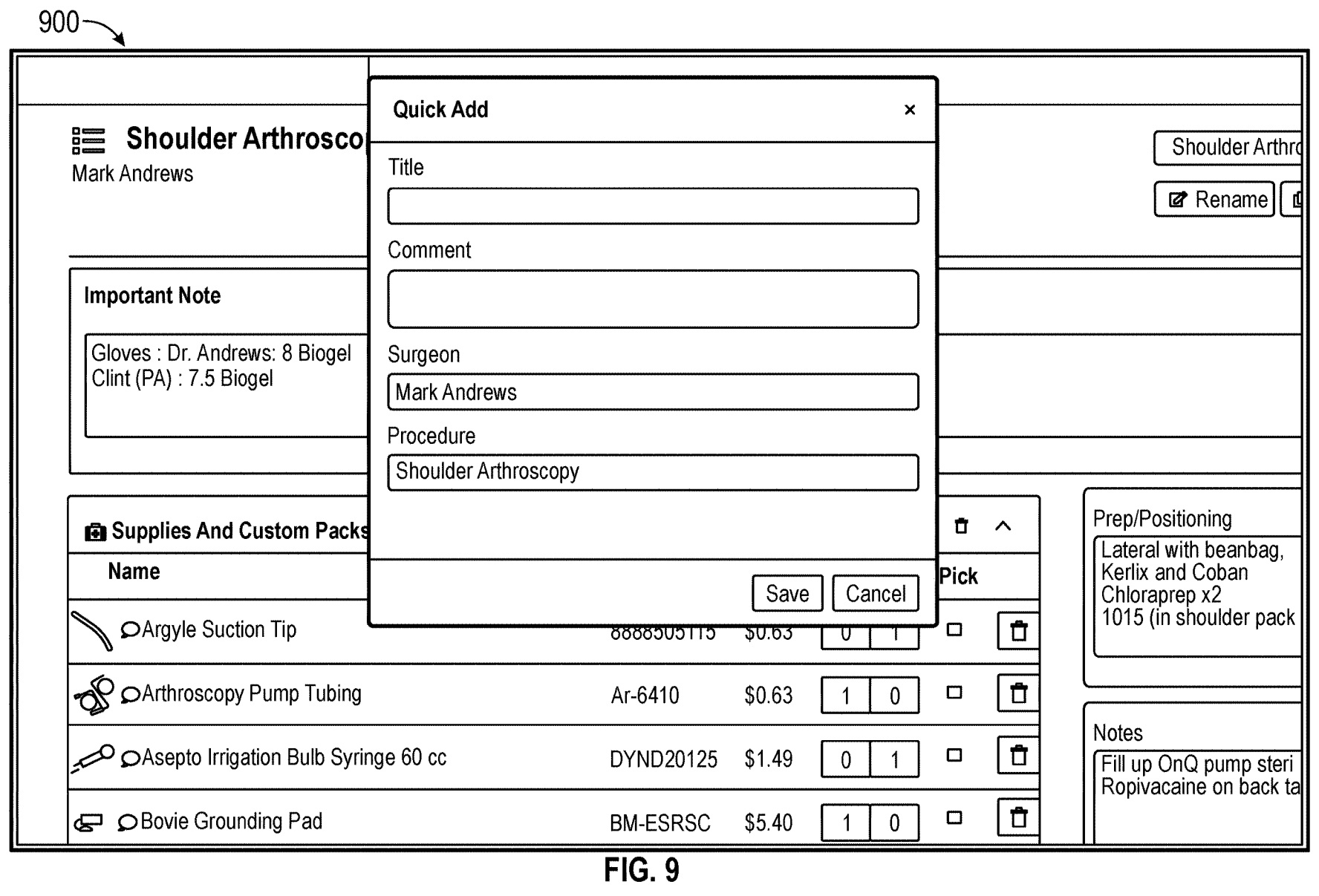

FIG. 9 is a screenshot of an example user interface 900 for quickly adding item selections to an aggregated data form. The data aggregation platform 102 enables a user to quickly add a note or item to an existing aggregated data form. The data aggregation platform 102 records the comment and may provide a form of knowledge capture. The user may later review the comments and make changes, then mark the notification or comment as being resolved.

The data aggregation server 104 may implement machine learning and tagging to extract the actions that need to be taken and present those actions as options for the user to accept as changes to the aggregated data form. This may be done rather than having the user evaluate the requested change. This recognition includes identifying the practitioner and procedure(s) from the freeform text of the comment.

Figure 10:
FIG. 10 is a screenshot of an example user interface for building an aggregated data form.

FIG. 10 is a screenshot of an example user interface 1000 for building an aggregated data form. The data aggregation platform 102 enables users to specify the organization and layout of the aggregated data form along with the number of columns of information on the aggregated data form, and what data should be associated with those columns of information. A facility may request a certain layout for aggregated data forms at that facility, and the requested layout will be propagated to all cards that that facility. This ensures the cards can be easily read and digested by facility personnel when gathering items for a procedure. The layout for an aggregated data form may be different on the practitioner's end versus the facility's end. Different accounts within one facility may request different layouts for the aggregated data forms used at that facility.

Figure 11:
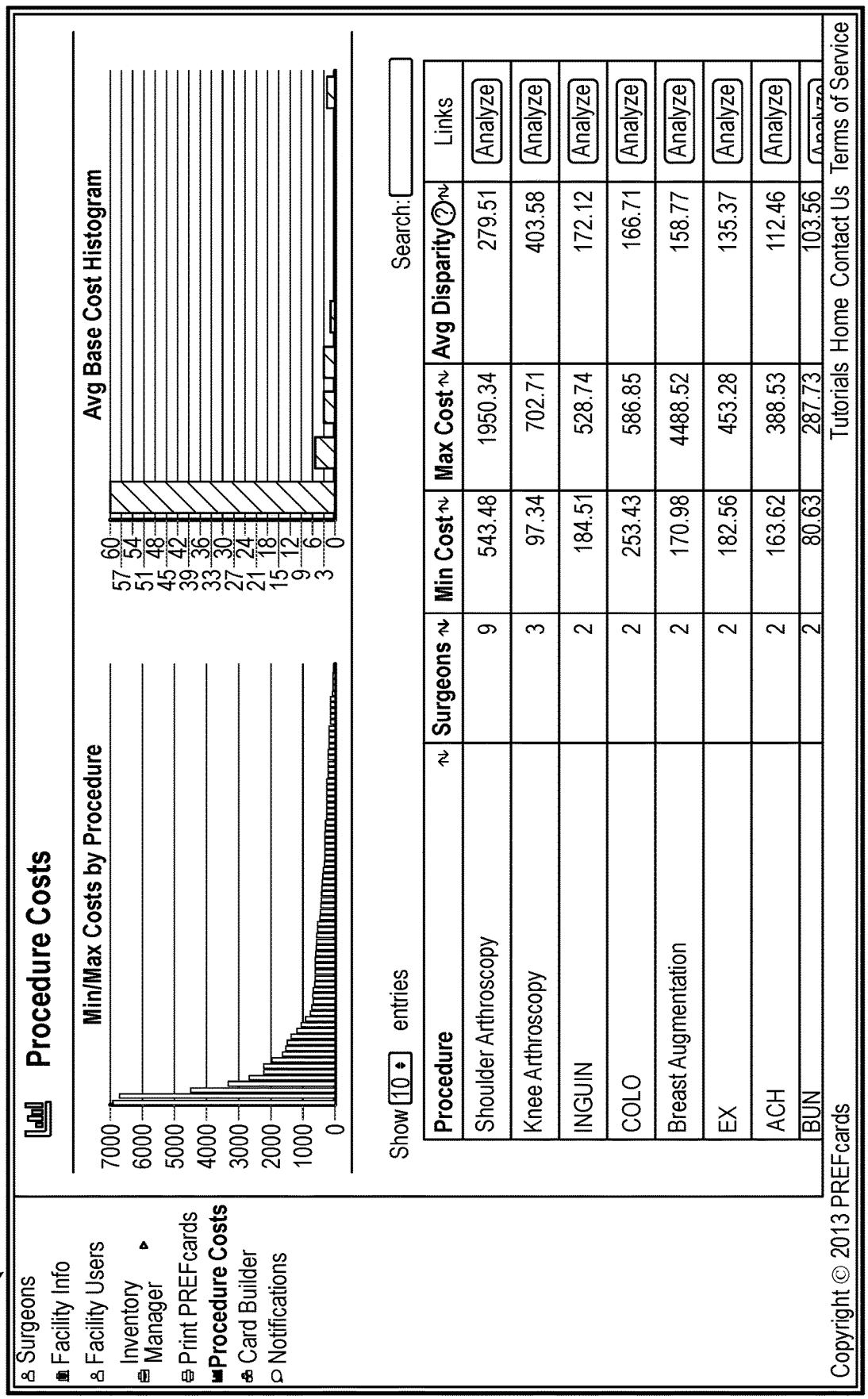
FIG. 11 is a screenshot of an example user interface for calculating predicted procedure costs based on items selected on an aggregated data form.

FIG. 11 is a screenshot of an example user interface 1100 for calculating predicted procedure costs based on items selected on an aggregated data form. The data aggregation platform 102 calculates the minimum and maximum predicted cost for performing a procedure based at least in part on the items selected in the associated aggregated data form. The predicted cost may be based on real-time data received from invoicing and disbursement tracking 112, global data 110, and or item catalog 108 as discussed herein.

The minimum cost is the sum of the costs of all items on the aggregated data form which are marked as open, indicating that the user preparing for the procedure should have the items open and ready to go for the practitioner. If the item is opened, it cannot be placed back into the stock room to be used on a different procedure. The maximum cost is calculated by adding up the costs of all open and hold items, which reflects 100% utilization of the items requested to be pulled for the procedure. This is not truly a maximum cost, as anything could happen during a procedure that could require additional items that were not on the original card but having a large difference between the minimum and maximum costs is usually an indicator that the practitioner is preparing for additional items that may need to be used but is being prudent in the number of those items that they open before the case starts. FIG. 11 presents all procedures across all practitioners at the facility. The table groups the practitioners by procedure and calculates the minimum cost across all the practitioners' minimum costs. The maximum cost in the table is the maximum across all practitioners' maximum costs.

FIG. 12 is a screenshot of an example user interface 1200 for providing cost-variation data for a certain procedure. The data aggregation platform 102 may provide cost analysis per-practitioner at a certain facility, within a healthcare network, within a healthcare system, within a geographic region, and so forth. The cost analysis data may be scrubbed such that all cost information is anonymous and does not reveal the practitioner or facility where the procedure was performed. The cost analysis may indicate the name of the practitioner and/or the facility where the procedure was performed (as illustrated in FIG. 12). The cost analysis may be based on the items selected in the aggregated data forms for each of the listed practitioners. The cost analysis may be broken down for each procedure and/or for each practitioner across all procedures performed by that practitioner.

FIG. 12 reflects a drill-down view of FIG. 11, wherein a single row of data from FIG. 11 is illustrated for an individual practitioner/procedure combination that make up that row's constituent members. The screenshot illustrates in the charts whether there are any outliers in the data, as well as the magnitude of variance in the table below.

Figure 13:
FIG. 13 is a screenshot of an example user interface for selecting, printing, viewing, and communicating aggregated data forms.

FIG. 13 is a screenshot of an example user interface 1300 for selecting, printing, viewing, and communicating aggregated data forms. The print page provides a plurality of aggregated data forms that may be viewed by the user associated with the account. The data aggregation server 104 may communicate with a facility and/or practitioner to identify which procedures are scheduled to be performed in an upcoming time period, and the data aggregation platform 104 may provide the applicable aggregated data forms that will need to be reference during the upcoming time period. In an implementation, the data aggregation server 104 automatically pulls all aggregated data forms for procedures schedule to be performed the following day and provides those preferences cards to the applicable persons at the facility where the procedures will be performed.

FIG. 14 is a screenshot of an applicable user interface and virtual file 1400 output by the data aggregation server 104. The example screenshot illustrates a document comprising an aggregated data form for a shoulder arthroscopy procedure to be performed by ANDREWS, MARK. The aggregated data form includes a QR code that may be scanned by a system at the facility. The QR may provide instructions to an inventory management solution 106 that indicates with items should be selected and retrieved for the procedure. The QR may include computer-based instructions indicating that a robotic component of the inventory management solution 106 should retrieve the items listed on the aggregated data form.

FIG. 15 is a screenshot of an example user interface 1500 of the data aggregation platform 102. The screenshot illustrates inventory management data indicating the names, reference identifiers, cost, status, category, and manufacturer for certain items. The items listed in the screenshot may be items used by a certain practitioner or facility, items owned by a facility, items that need to be purchased by a facility, items that will be used in upcoming scheduled procedures, and so forth. The list of items is hosted on the data aggregation server 104 and may additionally include items populated from an internal or external connection to software systems run by a facility inventory management system or item catalog.

FIG. 16 is a screenshot of an example user interface 1600 of the data aggregation platform 102. The screenshot indicates notifications that may be generated by a practitioner and/or facility and transmitted to other accounts. In the example notification, a practitioner (Mark Andrews) is requesting a certain glove size for all procedures moving forward. The component illustrated in FIG. 16 allows for review of comments captured in the knowledge capture interface illustrated in FIG. 9. These comments can then be marked as resolved once the required changes are made to the cards indicated.

FIGS. 17A-17E illustrate screenshots of an example user interface 1700 for presenting an aggregated data form. The screenshots illustrated in FIG. 17A-17E capture the example aggregated data form in order from top to bottom. The organization and layout of the user interface 1700 may be altered based on the preference of the healthcare administrator or provider, surgeon, surgical staff, and so forth.

Figure 17A:
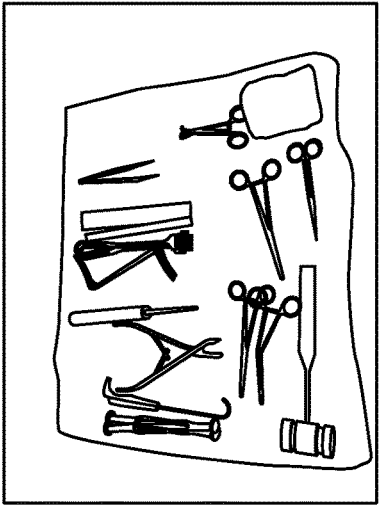
FIG. 17A is a screenshot of a portion of an example user interface for presenting a virtual file output for an aggregated data form, wherein the portion illustrates the type of surgery, significant notes, an image of requested tools, and a partial listing of requested supplies.

The user interface 1700 includes a title of the surgery. In this case, the title indicates that the aggregated data form includes instructions for a total knee arthroplasty. The aggregated data form is intended for Surging Surgery Center with surgeon Ronald Hillock. The user interface 1700 includes a means for downloading 1704 the aggregated data form. The downloaded aggregated data form may be converted to a desired file format, such as a PDF, word document, plain text, and so forth. The user interface 1700 includes a second for providing important notes 1706 about the surgery. The important notes 1706 may be provided by the surgeon, surgical center, healthcare administrator, and so forth. The important notes 1706 may be surgery-specific, surgeon-specific, patient-specific, surgical center-specific, and so forth. The important notes 1706 may recite different information for different surgeries performed by the same surgeon at the same surgical center. The user interface 1700 includes a listing of supplies 1708. The supplies 1708 may include listing of custom packs of supplies as illustrated in FIG. 17A. The user interface 1700 includes surgical setup images 1710 for illustrating how the surgeon or surgical center prefers that the tools be organized and prepared prior to surgery. In FIG. 17A, the surgical setup images include the illustration of a Mayo Stand that depicts a collection of tools laid out on the Mayo Stand.

Turning now to FIG. 17B, the user interface 1700 includes further listings of supplies 1708 needed for the surgery. The user interface 1700 includes additional surgical setup images 1710, and in the example illustrated in FIG. 17B, the surgical setup images 1710 include a depiction of a back table with an assortment of tools and supplies set up on the back table. The user interface 1700 includes a preparation and positioning 1712 section for providing information about how the patient should be prepared for surgery. The user interface 1700 includes a medications and dressing 1714 section for providing information about how the patient should be prepared for surgery and dressed after surgery.

Turning now to FIG. 17C, the user interface 1700 includes further listings of supplies 1708 needed for the surgery. The user interface 1700 includes further surgical setup images 1710 depicting how the operation room should be prepared for surgery. The surgical setup image 1710 illustrated in FIG. 17C depicts a complete room setup with a depiction of several tables comprising surgical tools and supplies. The user interface 1700 includes a requested music 1716 section providing the surgeon's requested music during the surgery.

Turning now to FIGS. 17D-17E, the user interface 1700 includes further listings of supplies 1708 needed for the surgery. The supplies 1708 may include, for example, supplies and custom packs, instruments, trays, equipment, gloves, sutures, implantable items, medications, and so forth. The listing of supplies 1708 may include an image of the requested item, a surgical center-specific price for the item, a predicted price for the item, a reference number for the item, and indication of how the item is priced (i.e., per-unit, per-bottle, and so forth), a quantity for how many of the requested item should be present in the surgery, an indication of how many of the requested item have been held or reserved for the surgery, and so forth.

The user interface 1700 is accessible by way of a web browser or application. The user interface 1700 enables a user to hover over a certain item and receive additional information about that item when the cursor is hovering over the item. In an example implementation, when a user hovers over a certain item, a popup may appear indicating whether the item is expensive. In an instance where the item is priced higher than usual, a popup may appear indicating that the specific item is expensive, and the user should consider holding that item rather than immediately opening the item. In some cases, it may be desirable to leave some items unopened until they are necessary during the surgery. In some cases, the item might not be opened, and then the patient and healthcare provider can save on the cost of the item.

The user interface 1700 includes hyperlinks enabling a user to gather additional information about a certain category. The surgical setup images 1710 include a hyperlink for viewing a high-resolution version of the image. The listing of supplies 1708 include hyperlinks for expanding the item to view more information about the item; viewing a database output indicating how many of the certain item is in-stock at the surgical center; purchasing the requested item directly from a supplier; or requesting the item from a pharmacy or other office at the surgical center. The user interface 1700 includes hyperlinks for accessing additional information about, for example, the names of the items, the cost of the items, the reference numbers for the items, the unit-types for the items, whether a certain quantity of the items are open, and whether a certain quantity of the items are held.

The user interface 1700 includes a means to directly contact any of the surgeon, surgical staff, surgical center, healthcare provider, and so forth. The contact information may include a means to initiate a telephone call, video chat, or Internet-based phone call. The contact information may include a means to email, text message, or otherwise communicate with any listed person. The contact information may include information about the patient.

Figure 18A:
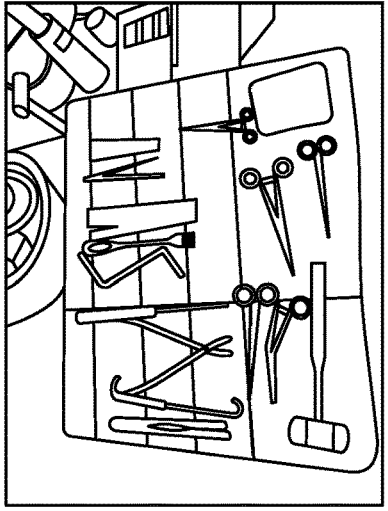
FIG. 18A is a screenshot of a virtual file output for presenting an aggregated data form.

FIGS. 18A-18B illustrate screenshots of an example virtual file 1800 for presenting an aggregated data form. The virtual file 1800 may be downloaded from the user interface 1700. The example virtual file illustrated in FIGS. 18A-18B includes the same information viewable in the user interface 1700 illustrated in FIGS. 17A-17E. The virtual file 1800 includes a unique code 1818. The unique code 1818 may include a QR code as illustrated in FIGS. 18A-18B or may include some other unique code.

The unique code 1818 may be any scannable figure or code that is readable by the data aggregation module 114 such as a mobile phone, camera, or other device comprising an image sensor. In an embodiment, the unique code 1818 is a two-dimensional barcode such as a quick response (QR) code. The two-dimensional barcode can be digitally scanned by a camera or other sensor on the data aggregation module 114. The unique code 1818 may include multiple squares that can be read by the image sensor of the data aggregation module 114.

In an embodiment where the unique code 1818 is a QR code, the code includes three large squares (the three large squares can be seen in the upper-left, lower-left, and upper-right corners of the example unique code 1818 shown in FIGS. 18A-18B) that serve as alignment targets while a smaller square in a remaining corner of the unique code 1818 (the smaller square can be seen near the lower-right corner of the example unique code 1818 shown in FIGS. 18A-18B) serves to normalize the angle with which the image sensor hits the unique code 1818. The remaining area of the unique code 1818 is the actual data that is converted into binary code by the data aggregation module 114. The unique code 1818 may include many characters worth of data. In an example where the unique code 1818 is a 117-pixel square, the code may hold 1852 characters of data.

In an embodiment, an image sensor of the data aggregation module 114 is directed to scan the unique code 1818, and the unique code 1818 includes instructions for the data aggregation module 114 to connect to the data aggregation server 104. A processor of the data aggregation module 114 may execute the instructions stored in the unique code 1818 to automatically connect to the data aggregation server 104. In various implementations, the data aggregation module 114 may request permission from a user and/or query the user whether the data aggregation module 114 should connect to the media server 104. In an embodiment, automatically connecting to the data aggregation server 104 brings the data aggregation platform 102 up on the data aggregation module 114 in an application, program, webpage, or by some other suitable means.

When a user connects to the data aggregation platform 102 upon scanning the unique code 1818, the user may be directed to the user interface 1700 such as the one illustrated in FIGS. 17A-17E. The user may then view details about the aggregated data form, propose amendments to the aggregated data form, correct errors in the aggregated data form, initiate contact with one or more persons associated with the aggregated data form, and so forth. The user may additionally view other aggregated data forms saved on the data aggregation server 104 associated with the same surgeon, surgical center, healthcare network, healthcare facility, and so forth. The user may view public aggregated data forms posted to the data aggregation server 104. The user may select a case, build out the card, add or remove items to the card, document usage of the card, enter surgical notes, and so forth.

FIG. 19 is a schematic flow chart diagram of a method 1900 for performing file analysis and classifying information in data buckets associated with an aggregated data form. The method 1900 may be performed by a computing device, such as the data aggregation server 104 and/or computing components associated with the data aggregation platform 102 as described herein.

The method 1900 begins and a data ingestion engine ingests at 1902 an unstructured file comprising text. The unstructured file may include, for example, an image, video file, scan, PDF, Microsoft® Word document, and so forth. The method 1900 continues and a computing processor provides at 1904 the unstructured file to a file analysis machine learning algorithm configured to execute optical character recognition processing to identify one or more textual characters in the unstructured file. The method 1900 continues and a computing processor assigns at 1906 the one or more identified textual characters to a data bucket associated with an aggregated data form. The method 1900 continues and a computing processor generates at 1908 a virtual file comprising information from the aggregated data form, wherein the virtual file comprises structured data and unstructured data.

Figure 20:
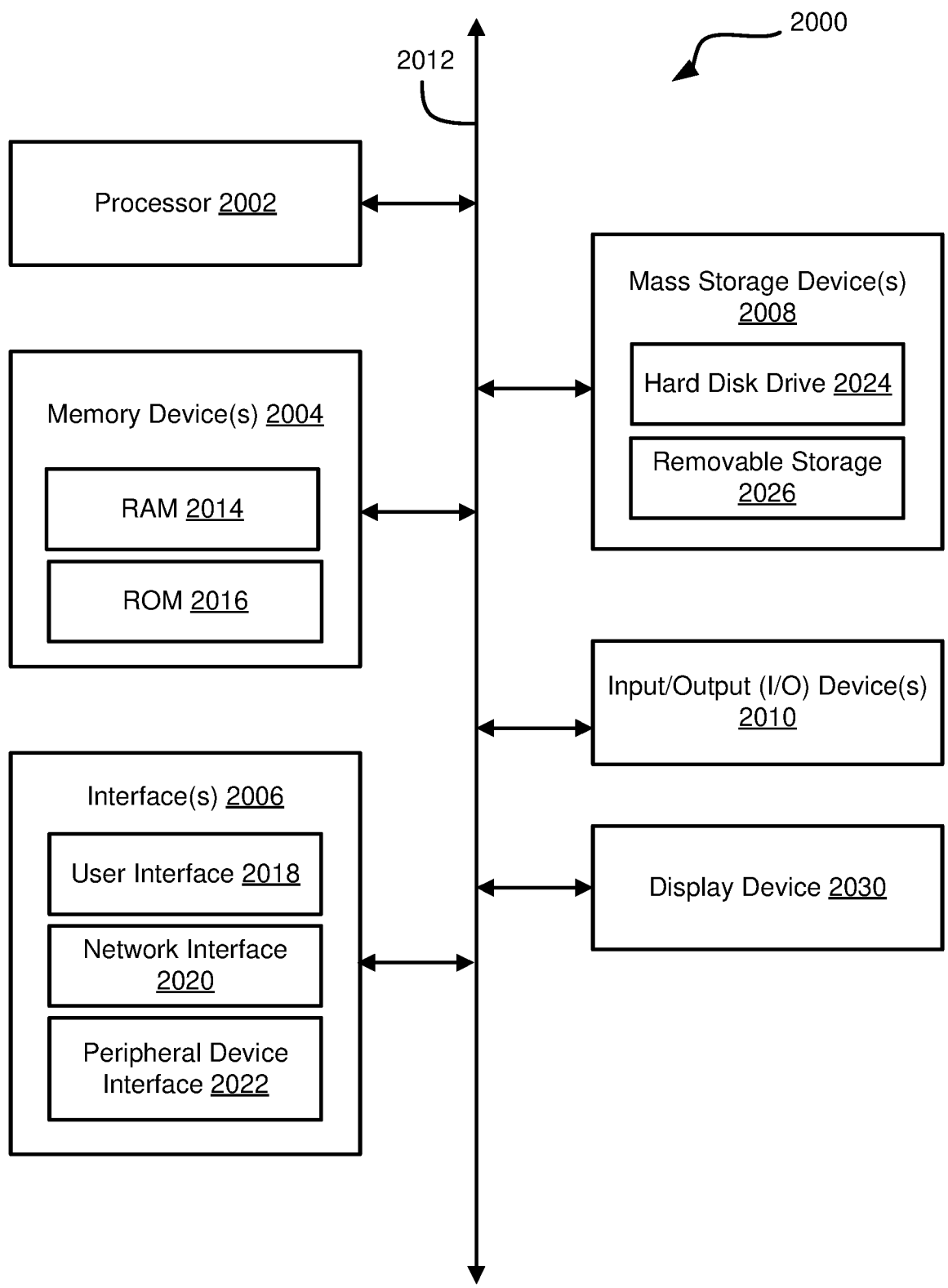
FIG. 20 is a schematic diagram illustrating components of an example computing device.

Referring now to FIG. 20, a block diagram of an example computing device 2000 is illustrated. Computing device 2000 may be used to perform various procedures, such as those discussed herein. Computing device 2000 can perform various monitoring functions as discussed herein, and can execute one or more application programs, such as the application programs or functionality described herein. Computing device 2000 can be any of a wide variety of computing devices, such as a desktop computer, in-dash computer, vehicle control system, a notebook computer, a server computer, a handheld computer, tablet computer and the like.

Computing device 2000 includes one or more processor(s) 2004, one or more memory device(s) 2004, one or more interface(s) 2006, one or more mass storage device(s) 2008, one or more Input/output (I/O) device(s) 2010, and a display device 2030 all of which are coupled to a bus 2012. Processor(s) 2004 include one or more processors or controllers that execute instructions stored in memory device(s) 2004 and/or mass storage device(s) 2008. Processor(s) 2004 may also include various types of computer-readable media, such as cache memory.

Memory device(s) 2004 include various computer-readable media, such as volatile memory (e.g., random access memory (RAM) 2014) and/or nonvolatile memory (e.g., read-only memory (ROM) 2016). Memory device(s) 2004 may also include rewritable ROM, such as Flash memory.

Mass storage device(s) 2008 include various computer readable media, such as magnetic tapes, magnetic disks, optical disks, solid-state memory (e.g., Flash memory), and so forth. As shown in FIG. 20, a particular mass storage device 2008 is a hard disk drive 2024. Various drives may also be included in mass storage device(s) 2008 to enable reading from and/or writing to the various computer readable media. Mass storage device(s) 2008 include removable media 2026 and/or non-removable media.

I/O device(s) 2010 include various devices that allow data and/or other information to be input to or retrieved from computing device 2000. Example I/O device(s) 2010 include cursor control devices, keyboards, keypads, microphones, monitors or other display devices, speakers, printers, network interface cards, modems, and the like.

Display device 2030 includes any type of device capable of displaying information to one or more users of computing device 2000. Examples of display device 2030 include a monitor, display terminal, video projection device, and the like.

Interface(s) 2006 include various interfaces that allow computing device 2000 to interact with other systems, devices, or computing environments. Example interface(s) 2006 may include any number of different network interfaces 2020, such as interfaces to local area networks (LANs), wide area networks (WANs), wireless networks, and the Internet. Other interface(s) include user interface 2018 and peripheral device interface 2022. The interface(s) 2006 may also include one or more user interface elements 2018. The interface(s) 2006 may also include one or more peripheral interfaces such as interfaces for printers, pointing devices (mice, track pad, or any suitable user interface now known to those of ordinary skill in the field, or later discovered), keyboards, and the like.

Bus 2012 allows processor(s) 2004, memory device(s) 2004, interface(s) 2006, mass storage device(s) 2008, and I/O device(s) 2010 to communicate with one another, as well as other devices or components coupled to bus 2012. Bus 2012 represents one or more of several types of bus structures, such as a system bus, PCI bus, IEEE bus, USB bus, and so forth.

For purposes of illustration, programs and other executable program components are shown herein as discrete blocks, such as block 302 for example, although it is understood that such programs and components may reside at various times in different storage components of computing device 2000 and are executed by processor(s) 2002. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

Examples

The following examples pertain to further implementations of the disclosure.

Example 1 is a method. The method includes receiving an indication of a surgical procedure to be performed. The method includes identifying one or more suggested items to be used during the surgical procedure. The method includes generating an aggregated data form for the surgical procedure, wherein the aggregated data form comprises a listing of the one or more suggested items.

Example 2 is a method as in Example 1, further comprising generating a unique code associated with the surgical procedure, wherein the unique code is scannable and comprises instructions for connecting to a server supporting the aggregated data form.

Example 3 is a method as in any of Examples 1-2, wherein identifying the one or more suggested items comprises providing the surgical procedure to a neural network configured to predict the one or more suggested items based on a plurality of surgical procedures performed by a plurality of healthcare providers.

Example 4 is a method as in any of Examples 1-3, wherein the aggregated data form comprising real-time pricing for each of the one or more suggested items.

Example 5 is a method as in any of Examples 1-4, further comprising communicating the aggregated data form to an automated billing system for identifying one or more items used during the surgical procedure.

Example 6 is a method as in any of Examples 1-5, further comprising associating the aggregated data form with a healthcare provider and providing read and write access on the aggregated data form to the healthcare provider.

Example 7 is a method as in any of Examples 1-6, further comprising associating one or more surgical setup images with the aggregated data form, wherein the surgical setup images comprise a depiction of how items should be arranged prior to the surgical procedure.

Example 8 is a method as in any of Examples 1-7, further comprising determining a minimum quantity and a maximum quantity for each of the one or more suggested items.

Example 9 is a method of collecting, aggregating, and analyzing data, the method comprising. The method includes ingesting an unstructured file comprising text. The method includes providing the unstructured file to a file analysis machine learning algorithm configured to execute optical character recognition processing to identify one or more textual characters in the unstructured file. The method includes assigning the one or more identified textual characters to a data bucket associated with an aggregated data form. The method includes generating a virtual file comprising information from the aggregated data form, wherein the virtual file comprises structured data and unstructured data.

Example 10 is a method as in Example 9, wherein: the aggregated data form comprises a plurality of independent data buckets; each of the plurality of independent data buckets is configured to receive data of a certain file type and a certain content; and the process of assigning the one or more identified textual characters to the data bucket associated with the aggregated data form comprises identifying a correct data bucket for the one or more identified textual characters.

Example 11 is a method as in any of Examples 9-10, wherein generating the virtual file comprises generating a summary file comprising the structured data and the unstructured data stored in the aggregated data form, wherein the summary file comprises one or more of a collection of data accessible on a user interface, a collection of data accessible on a web page, or a file stored in a portable document format.

Example 12 is a method as in any of Examples 9-11, further comprising communicating with a web scraping module, wherein the web scraping module is configured to extract structured data from one or more web pages, wherein the structured data comprises information regarding one or more products, the information comprising one or more of a name, unique product code, regulatory approval status, current price, current availability, or safety rating.

Example 13 is a method as in any of Examples 9-12, wherein the aggregated data form comprises information for a surgical preference card, and wherein the method further comprises: storing a master aggregated data form associated with a healthcare system, wherein the healthcare system comprises a plurality of surgical facilities; storing a plurality of facility aggregated data forms, wherein each of the plurality of facility aggregated data forms is associated with one facility of the plurality of surgical facilities in the healthcare system; updating each of the plurality of facility aggregated data forms when the master aggregated data form is updated.

Example 14 is a method as in any of Examples 9-13, wherein the optical character recognition processing performed by the file analysis machine learning algorithm comprises: identifying a boundary between a bright pixel region and a dark pixel region; classifying the bright pixel region as background; processing the dark pixel region to identify a textual character, wherein the textual character comprises one or more of a letter, number, emoji, or punctuation character.

Example 15 is a method as in any of Examples 9-14, wherein the aggregated data form comprises a plurality of data buckets, and wherein one or more of the plurality of data buckets is a required data bucket that must be filled with data for the aggregated data form to be complete, and wherein the method further comprises: determining whether the aggregated data form is complete based on whether each of the required data buckets is filled; and in response to determining that each of the required data buckets is filled, generating a message querying a user whether the aggregated data bucket is complete.

Example 16 is a method as in any of Examples 9-15, wherein the aggregated data form comprises digital information for a surgical preference card, and wherein the unstructured file comprises a depiction of a completed preference card, and wherein the depiction of the completed preference card comprises one or more of: an image, scan, or portable document format (PDF) of a handwritten surgical preference card; an image, scan, or PDF of a printed surgical preference card; or an image, scan, or PDF of a digital surgical preference card.

Example 17 is a method as in any of Examples 9-16, further comprising rendering a user interface accessible to a user, wherein the user interface comprises: a dropdown listing of a plurality of items listed on a surgical preference card, wherein the dropdown listing comprises functionality enabling the user to expand or diminish the dropdown listing; a hyperlink associated with one or more of the plurality of items in the dropdown listing, wherein the hyperlink directs to a means for ordering the corresponding item; a text box associated with one or more of the plurality of items in the dropdown listing, wherein the text box comprises a means for a user to input a quantity of the corresponding item; and a button associated with one or more of the plurality of items in the dropdown listing, wherein the button comprises a means for a user to delete the corresponding item from the surgical preference card.

Example 18 is a method as in any of Examples 9-17, further comprising: determining whether the aggregated data form is a master aggregated data form, or a facility aggregated data form; in response to determining the aggregated data form is a master aggregated data form, identifying one or more facility aggregated data forms that are associated with the master aggregated data form; determining whether any of the one or more facility aggregated data forms is inconsistent with information stored on the master aggregated data form; and in response to determining that at least one of the one or more facility aggregated data forms is inconsistent with the master aggregated data form, updating the at least one facility aggregated data form to comprise the same data associated with the master aggregated data form.

Example 19 is a system comprising one or more processors for executing instructions stored in non-transitory computer readable storage medium, wherein the instructions comprising any of the method steps described in connection with Examples 1-19.

Example 20 is non-transitory computer readable storage medium storing instructions to be executed by one or more processors, the instructions comprising any of the method steps described in connection with Examples 1-19.

Example 21 is means for performing any of the method steps described in connection with Examples 1-19.

Example 22 is a system. The system includes means for ingesting an unstructured file comprising text. The system includes means for providing the unstructured file to a file analysis machine learning algorithm configured to execute optical character recognition processing to identify one or more textual characters in the unstructured file. The system includes means for assigning the one or more identified textual characters to a data bucket associated with an aggregated data form. The system includes means for generating a virtual file comprising information from the aggregated data form, wherein the virtual file comprises structured data and unstructured data.

Example 23 is a system as in Example 22, wherein: the aggregated data form comprises a plurality of independent data buckets; each of the plurality of independent data buckets is configured to receive data of a certain file type and a certain content; and the means for assigning the one or more identified textual characters to the data bucket associated with the aggregated data form comprises means for identifying a correct data bucket for the one or more identified textual characters.

Example 24 is a system as in any of Examples 22-23, wherein the means for generating the virtual file comprises means for generating a summary file comprising the structured data and the unstructured data stored in the aggregated data form, wherein the summary file comprises one or more of a collection of data accessible on a user interface, a collection of data accessible on a web page, or a file stored in a portable document format.

Example 25 is a system as in any of Examples 22-24, further comprising means for communicating with a web scraping module, wherein the web scraping module is configured to extract structured data from one or more web pages, wherein the structured data comprises information regarding one or more products, the information comprising one or more of a name, unique product code, regulatory approval status, current price, current availability, or safety rating.

Example 26 is a system as in any of Examples 22-25, wherein the aggregated data form comprises information for a surgical preference card, and wherein the system further comprises: means for storing a master aggregated data form associated with a healthcare system, wherein the healthcare system comprises a plurality of surgical facilities; means for storing a plurality of facility aggregated data forms, wherein each of the plurality of facility aggregated data forms is associated with one facility of the plurality of surgical facilities in the healthcare system; and means updating each of the plurality of facility aggregated data forms when the master aggregated data form is updated.

Example 27 is a system as in any of Examples 22-26, wherein the file analysis machine learning algorithm comprises: means for identifying a boundary between a bright pixel region and a dark pixel region; means for classifying the bright pixel region as background; and means for processing the dark pixel region to identify a textual character, wherein the textual character comprises one or more of a letter, number, emoji, or punctuation character.

Example 28 is a system as in any of Examples 22-27, wherein the aggregated data form comprises a plurality of data buckets, and wherein one or more of the plurality of data buckets is a required data bucket that must be filled with data for the aggregated data form to be complete, and wherein the system further comprises: means for determining whether the aggregated data form is complete based on whether each of the required data buckets is filled; and means for generating a message querying a user whether the aggregated data bucket is complete in response to determining that each of the required data buckets is filled.

Example 29 is a system as in any of Examples 22-28, wherein the aggregated data form comprises digital information for a surgical preference card, and wherein the unstructured file comprises a depiction of a completed preference card, and wherein the depiction of the completed preference card comprises one or more of: an image, scan, or portable document format (PDF) of a handwritten surgical preference card; an image, scan, or PDF of a printed surgical preference card; or an image, scan, or PDF of a digital surgical preference card.

Example 30 is a system as in any of Examples 22-29, further comprising means for rendering a user interface accessible to a user, wherein the user interface comprises: a dropdown listing of a plurality of items listed on a surgical preference card, wherein the dropdown listing comprises functionality enabling the user to expand or diminish the dropdown listing; a hyperlink associated with one or more of the plurality of items in the dropdown listing, wherein the hyperlink directs to a means for ordering the corresponding item; a text box associated with one or more of the plurality of items in the dropdown listing, wherein the text box comprises a means for a user to input a quantity of the corresponding item; and a button associated with one or more of the plurality of items in the dropdown listing, wherein the button comprises a means for a user to delete the corresponding item from the surgical preference card.

Example 31 is a system as in any of Examples 22-30, further comprising: means for determining whether the aggregated data form is a master aggregated data form, or a facility aggregated data form; means for identifying one or more facility aggregated data forms that are associated with the master aggregated data form in response to determining the aggregated data form is a master aggregated data form; means for determining whether any of the one or more facility aggregated data forms is inconsistent with information stored on the master aggregated data form; and means for updating the at least one facility aggregated data form to comprise the same data associated with the master aggregated data form in response to determining that at least one of the one or more facility aggregated data forms is inconsistent with the master aggregated data form.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, mini-computers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the embodiments and implementations discussed above may comprise computer hardware, software, firmware, or any combination thereof to perform at least a portion of their functions. For example, an embodiment and an implementation may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program items comprising such logic (e.g., in the form of software) stored on any computer useable medium. Such software, when executed in one or more data processing devices, causes a device to operate as described herein.

While various embodiments of the present disclosure have been described above, it should be understood they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible considering the above teaching. Further, it should be noted that any or all the alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method of collecting, aggregating, and analyzing data, the method comprising:
    ingesting an unstructured file comprising text;
    mapping the unstructured file to a primary aggregated data form, wherein the primary aggregated data form is mapped to a tenant on a cloud-based database;
    creating a unique user pool for the primary aggregated data form to provide data isolation security to the primary aggregated data form, wherein users within the unique user pool have permissions to access the primary aggregated data form;
    translating the unstructured file to a computer-readable file by causing a file analysis machine learning algorithm to execute optical character recognition processing on the unstructured file to identify textual characters in the unstructured file;
    classifying content of a plurality of words or phrases within the computer-readable file by cross-referencing the plurality of words or phrases against known vocabulary, wherein the plurality of words or phrases comprises a name of a device;
    scraping web data from a webpage by communicating directly with the webpage and executing a web script to render the webpage as a simulated user interaction, wherein the scraped web data pertains to the device;
    comparing the scraped web data to applicable stored data to determine whether a discrepancy exists between the scraped web data and the applicable stored data, wherein the applicable stored data pertains to the device;
    in response to identifying the discrepancy between the scraped web data and the applicable stored data, resolving the discrepancy by updating the applicable stored data to comprise the scraped web data;
    assigning the plurality of words or phrases from the computer-readable file to one or more data buckets associated with the primary aggregated data form based on the content classification, wherein the primary aggregated data form is stored on the cloud-based database, and wherein the primary aggregated data form comprises at least one device data bucket assigned to receive the name of the device;
    replicating the primary aggregated data form to generate one or more facility aggregated data forms, wherein each of the one or more facility aggregated data forms is customizable relative to the primary aggregated data form, and wherein each of the one or more facility aggregated data forms is stored on the database;
    generating a summary file comprising information from the primary aggregated data form, wherein the summary file comprises structured data and unstructured data;
    identifying a facility where the summary file will be utilized;
    retrieving the name of the device from the device data bucket for the aggregated data form;
    cross-referencing the name of the device against the applicable stored data pertaining to the device to identify one or more products associated with the device;
    electronically communicating with an inventory management solution associated with the facility to determine whether any of the one or more products is available at the facility; and
    electronically communicating with an invoicing system associated with the facility to determine an itemized cost of at least a portion of the one or more products when utilized at the facility.

2. The method of claim 1, wherein the primary aggregated data form comprises a plurality of independent data buckets;
    wherein each of the plurality of independent data buckets is configured to receive data of a certain file type and a certain content; and
    wherein the process of assigning the name of the device to the at least one device data bucket comprises identifying a correct data bucket for the device.

3. The method of claim 1, wherein the summary file comprises one or more of a collection of data accessible on a user interface, a collection of data accessible on a web page, or a file stored in a portable document format.

4. The method of claim 1, wherein scraping the web data from the webpage comprises extracting structured data from the webpage, and wherein the scraped structured data comprises one or more of:

one or more products applicable to the name of the device;
regulatory approval status associated with the one or more products;
current pricing for the one or more products;
current availability for the one or more products; or
safety rating for the one or more products.

5. The method of claim 1, wherein the primary aggregated data form comprises information for a surgical preference card, and wherein the method further comprises:
storing the primary aggregated data form associated with a healthcare system, wherein the healthcare system comprises a plurality of surgical facilities;
storing a plurality of facility aggregated data forms, wherein each of the plurality of facility aggregated data forms is associated with one facility of the plurality of surgical facilities in the healthcare system; and
updating each of the plurality of facility aggregated data forms when the primary aggregated data form is updated.

6. The method of claim 1, wherein the optical character recognition processing performed by the file analysis machine learning algorithm comprises:
identifying a boundary between a bright pixel region and a dark pixel region;
classifying the bright pixel region as background; and
processing the dark pixel region to identify a textual character, wherein the textual character comprises one or more of a letter, number, emoji, or punctuation character.

7. The method of claim 1, wherein the primary aggregated data form comprises a plurality of data buckets, and wherein one or more of the plurality of data buckets is a required data bucket that must be filled with data for the aggregated data form to be complete, and wherein the method further comprises:
determining whether the primary aggregated data form is complete based on whether each of the required data buckets is filled; and
in response to determining that each of the required data buckets is filled, generating a message querying a user whether the primary aggregated data bucket is complete.

8. The method of claim 1, wherein the primary aggregated data form comprises digital information for a surgical preference card, and wherein the unstructured file comprises a depiction of a completed preference card, and wherein the depiction of the completed preference card comprises one or more of:
an image, scan, or portable document format (PDF) of a handwritten surgical preference card;
an image, scan, or PDF of a printed surgical preference card; or
an image, scan, or PDF of a digital surgical preference card.

9. The method of claim 1, further comprising rendering a user interface accessible to a user, wherein the user interface comprises:
a dropdown listing of a plurality of items listed on a surgical preference card, wherein the dropdown listing comprises functionality enabling the user to expand or diminish the dropdown listing;
a hyperlink associated with one or more of the plurality of items in the dropdown listing, wherein the hyperlink directs to a means for ordering the corresponding item;
a text box associated with one or more of the plurality of items in the dropdown listing, wherein the text box comprises a means for a user to input a quantity of the corresponding item; and
a button associated with one or more of the plurality of items in the dropdown listing, wherein the button comprises a means for a user to delete the corresponding item from the surgical preference card.

10. The method of claim 1, further comprising:
identifying one or more facility aggregated data forms that are associated with the primary aggregated data form;
determining whether any of the one or more facility aggregated data forms is inconsistent with information stored on the primary aggregated data form; and
in response to determining that at least one of the one or more facility aggregated data forms is inconsistent with the primary aggregated data form, updating the at least one facility aggregated data form to comprise the same data associated with the primary aggregated data form.

11. The method of claim 1, wherein generating the summary file further comprises generating a machine-readable code, and wherein the machine-readable code stores an address or uniform resource locator ("URL") for retrieving the summary file.

12. The method of claim 11, further comprising:
scanning the machine-readable code of the summary file;
retrieving the summary file based on the address or the URL stored in the machine-readable code;
reading the structured data stored on the summary file, wherein the structured data comprises a listing of products; and
communicating with the inventory management solution to automatically retrieve one or more products in the listing of products.

13. The method of claim 1, wherein the inventory management solution comprises one or more robotic components for tracking and disbursing products located at the facility.

14. The method of claim 1, further comprising:
identifying which of the one or more products comprises a lowest itemized price; and
automatically updating the summary file to comprise the identified product with the lowest itemized price.

15. The method of claim 14, further comprising:
receiving updated data applicable to the device, wherein the updated data is scraped from the webpage;
processing the updated data to determine whether any new product is associated with the device;
in response to identifying the new product, electronically communicating with the inventory management solution to determine whether the new product is available at the facility; and
in response to identifying the new product, electronically communicating with the invoicing system to determine an itemized cost of the new product when utilized at the facility.

16. The method of claim 1, wherein the aggregated data form is a data format comprising the one or more data buckets, and wherein each of the one or more data buckets is dedicated to storing a certain datatype or data content, and wherein the one or more data buckets comprises:
a supplies data bucket assigned to storing supplies information, wherein the supplies information comprises a name and unique reference identifier for a plurality of single use supplies to be used during a procedure;

an instruments data bucket assigned to storing instruments information, wherein the instruments information comprises a name for a plurality of multiple-use instruments to be used during the procedure;

a preparation data bucket assigned to storing preparation information comprising an indication of how a patient should be prepared for the procedure; and an unstructured data bucket assigned to storing one or more unstructured files to be associated with the procedure.

17. The method of claim 1, wherein the summary file is utilized to prepare for a procedure, and wherein the method further comprises calculating a total cost for performing the procedure based on an itemized facility-specific cost for each of a plurality of products to be utilized during the procedure, a labor cost for each of a plurality of personnel to work during the procedure, and a facility cost for utilizing the facility during the procedure.

18. The method of claim 1, wherein identifying the one or more products associated with the name of the device comprises querying a database to identify the one or more products associated with the name of the device;
wherein the method further comprises identifying a unique product code for each of the one or more products; and
wherein the database comprises information extracted by a web scraper.

19. The method of claim 1, further comprising providing the summary file to a predictive modeling neural network trained to suggest one or more additional products to be utilized during a procedure associated with the summary file.

20. A system for collecting, aggregating, and analyzing data, the system comprising one or more processors for executing instructions stored in non-transitory computer readable storage medium, the instructions comprising:
ingesting an unstructured file comprising text;
mapping the unstructured file to a primary aggregated data form, wherein the primary aggregated data form is mapped to a tenant on a cloud-based database;
creating a unique user pool for the primary aggregated data form to provide data isolation security to the primary aggregated data form, wherein users within the unique user pool have permissions to access the primary aggregated data form;
translating the unstructured file to a computer-readable file by causing a file analysis machine learning algorithm to execute optical character recognition processing on the unstructured file to identify textual characters in the unstructured file;
classifying content of a plurality of words or phrases within the computer-readable file by cross-referencing the plurality of words or phrases against known vocabulary, wherein the plurality of words or phrases comprises a name of a device;
scraping web data from a webpage by communicating directly with the webpage and executing a web script to render the webpage as a simulated user interaction, wherein the scraped web data pertains to the device;
comparing the scraped web data to applicable stored data to determine whether a discrepancy exists between the scraped web data and the applicable stored data, wherein the applicable stored data pertains to the device;
in response to identifying the discrepancy between the scraped web data and the applicable stored data, resolving the discrepancy by updating the applicable stored data to comprise the scraped web data;
assigning the plurality of words or phrases from the computer-readable file to one or more data buckets associated with the primary aggregated data form based on the content classification, wherein the primary aggregated data form is stored on the cloud-based database, and wherein the primary aggregated data form comprises at least one device data bucket assigned to receive the name of the device;
replicating the primary aggregated data form to generate one or more facility aggregated data forms, wherein each of the one or more facility aggregated data forms is customizable relative to the primary aggregated data form, and wherein each of the one or more facility aggregated data forms is stored on the database;
generating a summary file comprising information from the primary aggregated data form, wherein the summary file comprises structured data and unstructured data;
identifying a facility where the summary file will be utilized;
retrieving the name of the device from the device data bucket for the aggregated data form;
cross-referencing the name of the device against the applicable stored data pertaining to the device to identify one or more products associated with the device;
electronically communicating with an inventory management solution associated with the facility to determine whether any of the one or more products is available at the facility; and
electronically communicating with an invoicing system associated with the facility to determine an itemized cost of at least a portion of the one or more products when utilized at the facility.

21. The system of claim 20, wherein the primary aggregated data form comprises a plurality of independent data buckets;
wherein each of the plurality of independent data buckets is configured to receive data of a certain file type and a certain content; and
wherein the process of assigning the name of the device to the at least one device data bucket comprises identifying a correct data bucket for the device.

22. The system of claim 20, wherein the summary file comprises one or more of a collection of data accessible on a user interface, a collection of data accessible on a web page, or a file stored in a portable document format.

23. The system of claim 20, wherein the instructions are such that scraping the web data from the webpage comprises extracting structured data from the webpage, and wherein the scraped structured data comprises one or more of:
one or more products applicable to the name of the device;
regulatory approval status associated with the one or more products;
current pricing for the one or more products;
current availability for the one or more products; or
safety rating for the one or more products.

24. The system of claim 20, wherein the primary aggregated data form comprises information for a surgical preference card, and wherein the method further comprises:
storing the primary aggregated data form associated with a healthcare system, wherein the healthcare system comprises a plurality of surgical facilities;
storing a plurality of facility aggregated data forms, wherein each of the plurality of facility aggregated data forms is associated with one facility of the plurality of surgical facilities in the healthcare system; and updating each of the plurality of facility aggregated data forms when the primary aggregated data form is updated.

25. The system of claim 20, wherein the optical character recognition processing performed by the file analysis machine learning algorithm comprises:
   identifying a boundary between a bright pixel region and a dark pixel region;
   classifying the bright pixel region as background; and
   processing the dark pixel region to identify a textual character, wherein the textual character comprises one or more of a letter, number, emoji, or punctuation character.

26. The system of claim 20, wherein the primary aggregated data form comprises a plurality of data buckets, and wherein one or more of the plurality of data buckets is a required data bucket that must be filled with data for the aggregated data form to be complete, and wherein the method further comprises:
   determining whether the primary aggregated data form is complete based on whether each of the required data buckets is filled; and
   in response to determining that each of the required data buckets is filled, generating a message querying a user whether the primary aggregated data bucket is complete.

27. The system of claim 20, wherein the primary aggregated data form comprises digital information for a surgical preference card, and wherein the unstructured file comprises a depiction of a completed preference card, and wherein the depiction of the completed preference card comprises one or more of:
   an image, scan, or portable document format (PDF) of a handwritten surgical preference card;
   an image, scan, or PDF of a printed surgical preference card; or
   an image, scan, or PDF of a digital surgical preference card.

28. The system of claim 20, wherein the instructions further comprise rendering a user interface accessible to a user, wherein the user interface comprises:
   a dropdown listing of a plurality of items listed on a surgical preference card, wherein the dropdown listing comprises functionality enabling the user to expand or diminish the dropdown listing;
   a hyperlink associated with one or more of the plurality of items in the dropdown listing, wherein the hyperlink directs to a means for ordering the corresponding item;
   a text box associated with one or more of the plurality of items in the dropdown listing, wherein the text box comprises a means for a user to input a quantity of the corresponding item; and
   a button associated with one or more of the plurality of items in the dropdown listing, wherein the button comprises a means for a user to delete the corresponding item from the surgical preference card.

29. The system of claim 20, wherein the instructions further comprise:
   identifying one or more facility aggregated data forms that are associated with the primary aggregated data form;
   determining whether any of the one or more facility aggregated data forms is inconsistent with information stored on the primary aggregated data form; and
   in response to determining that at least one of the one or more facility aggregated data forms is inconsistent with the primary aggregated data form, updating the at least one facility aggregated data form to comprise the same data associated with the primary aggregated data form.

30. Non-transitory computer readable storage medium storing instructions for execution by one or more processors, the instructions comprising:
   ingesting an unstructured file comprising text;
   mapping the unstructured file to a primary aggregated data form, wherein the primary aggregated data form is mapped to a tenant on a cloud-based database;
   creating a unique user pool for the primary aggregated data form to provide data isolation security to the primary aggregated data form, wherein users within the unique user pool have permissions to access the primary aggregated data form;
   translating the unstructured file to a computer-readable file by causing a file analysis machine learning algorithm to execute optical character recognition processing on the unstructured file to identify textual characters in the unstructured file;
   classifying content of a plurality of words or phrases within the computer-readable file by cross-referencing the plurality of words or phrases against known vocabulary, wherein the plurality of words or phrases comprises a name of a device;
   scraping web data from a webpage by communicating directly with the webpage and executing a web script to render the webpage as a simulated user interaction, wherein the scraped web data pertains to the device;
   comparing the scraped web data to applicable stored data to determine whether a discrepancy exists between the scraped web data and the applicable stored data, wherein the applicable stored data pertains to the device;
   in response to identifying the discrepancy between the scraped web data and the applicable stored data, resolving the discrepancy by updating the applicable stored data to comprise the scraped web data;
   assigning the plurality of words or phrases from the computer-readable file to one or more data buckets associated with the primary aggregated data form based on the content classification, wherein the primary aggregated data form is stored on the cloud-based database, and wherein the primary aggregated data form comprises at least one device data bucket assigned to receive the name of the device;
   replicating the primary aggregated data form to generate one or more facility aggregated data forms, wherein each of the one or more facility aggregated data forms is customizable relative to the primary aggregated data form, and wherein each of the one or more facility aggregated data forms is stored on the database;
   generating a summary file comprising information from the primary aggregated data form, wherein the summary file comprises structured data and unstructured data;
   identifying a facility where the summary file will be utilized;
   retrieving the name of the device from the device data bucket for the aggregated data form;
   cross-referencing the name of the device against the applicable stored data pertaining to the device to identify one or more products associated with the device;

electronically communicating with an inventory management solution associated with the facility to determine whether any of the one or more products is available at the facility; and electronically communicating with an invoicing system associated with the facility to determine an itemized cost of at least a portion of the one or more products when utilized at the facility.

* * * * *